United States Patent
Ratz et al.

(10) Patent No.: US 11,324,591 B2
(45) Date of Patent: *May 10, 2022

(54) PROSTHESIS FOR ATRAUMATICALLY GRASPING INTRALUMENAL TISSUE AND METHODS OF DELIVERY

(71) Applicant: Edwards Lifesciences CardiAQ LLC, Irvine, CA (US)

(72) Inventors: J. Brent Ratz, Winchester, MA (US); Arshad Quadri, West Hartford, CT (US); Luca Pesce, Huntington Beach, CA (US)

(73) Assignee: Edwards Lifesciences CardiAQ LLC, Irvine, CA (US)

( * ) Notice: Subject to any disclaimer, the term of this patent is extended or adjusted under 35 U.S.C. 154(b) by 287 days.

This patent is subject to a terminal disclaimer.

(21) Appl. No.: 16/783,868

(22) Filed: Feb. 6, 2020

(65) Prior Publication Data

US 2020/0170788 A1 Jun. 4, 2020

Related U.S. Application Data

(63) Continuation of application No. 15/947,168, filed on Apr. 6, 2018, now Pat. No. 10,583,000, which is a (Continued)

(51) Int. Cl.
*A61F 2/24* (2006.01)

(52) U.S. Cl.
CPC .......... *A61F 2/2409* (2013.01); *A61F 2/2418* (2013.01); *A61F 2/24* (2013.01); *A61F 2/2457* (2013.01); *A61F 2220/0008* (2013.01)

(58) Field of Classification Search
CPC ........ A61F 2/24; A61F 2/2409; A61F 2/2418; A61F 2/2412; A61F 2/2457
See application file for complete search history.

(56) References Cited

U.S. PATENT DOCUMENTS 3,657,744 A 4/1972 Ersek
3,671,979 A 6/1972 Moulopoulos
(Continued)

FOREIGN PATENT DOCUMENTS

CA 2304325 A1 10/2000
CA 2827556 A1 7/2012
(Continued)

OTHER PUBLICATIONS

Backer, Ole De, MD, et al., "Percutaneous Transcatheter Mitral Valve Replacement—An Overview of Devices in Preclinical and Early Clinical Evaluation," Contemporary Reviews in Interventional Cardiology, Circ Cardiovasc Interv. 2014;7:400-409, Applicant believes this may have been available as early as Jun. 2014.

(Continued)

*Primary Examiner* — Seema Mathew
(74) *Attorney, Agent, or Firm* — Knobbe Martens Olson & Bear LLP

(57) ABSTRACT

A prosthesis can comprise an expandable frame, a plurality of distal anchors and a plurality of proximal anchors. The anchors can extend outwardly from the frame. The frame can be configured to radially expand and contract for deployment within a body cavity. The frame and anchors can have one of many different shapes and configurations. For example, when the frame is in an expanded configuration, the frame can have a larger cross-sectional dimension in a middle portion of the frame and a smaller cross-sectional dimension in a proximal portion and a distal portion of the frame, wherein the middle portion is between the proximal and distal portions. As another example, the anchors can have looped ends, the entire anchor may loop out from the frame.

20 Claims, 11 Drawing Sheets

Related U.S. Application Data continuation of application No. 14/197,690, filed on Mar. 5, 2014, now abandoned.

(60) Provisional application No. 61/782,707, filed on Mar. 14, 2013.

(56) References Cited

U.S. PATENT DOCUMENTS

| | | | |
|---|---|---|---|
| 3,739,402 A | 6/1973 | Cooley et al. |
| 4,056,854 A | 11/1977 | Boretos et al. |
| 4,079,468 A | 3/1978 | Liotta et al. |
| 4,204,283 A | 5/1980 | Bellhouse et al. |
| 4,222,126 A | 9/1980 | Boretos et al. |
| 4,265,694 A | 5/1981 | Boretos et al. |
| 4,339,831 A | 7/1982 | Johnson |
| 4,340,977 A | 7/1982 | Brownlee et al. |
| 4,470,157 A | 9/1984 | Love |
| 4,477,930 A | 10/1984 | Totten et al. |
| 4,490,859 A | 1/1985 | Black et al. |
| 4,553,545 A | 11/1985 | Maass et al. |
| 4,777,951 A | 10/1988 | Cribier et al. |
| 4,865,600 A | 9/1989 | Carpentier et al. |
| 4,994,077 A | 2/1991 | Dobben |
| 5,326,371 A | 7/1994 | Love et al. |
| 5,332,402 A | 7/1994 | Teitelbaum |
| 5,370,685 A | 12/1994 | Stevens |
| 5,411,552 A | 5/1995 | Andersen et al. |
| 5,415,667 A | 5/1995 | Frater |
| 5,545,214 A | 8/1996 | Stevens |
| 5,554,185 A | 9/1996 | Block et al. |
| 5,697,382 A | 12/1997 | Love et al. |
| 5,840,081 A | 11/1998 | Andersen et al. |
| 5,855,601 A | 1/1999 | Bessler et al. |
| 5,957,949 A | 9/1999 | Leonhardt et al. |
| 6,086,612 A | 7/2000 | Jansen |
| 6,113,631 A | 9/2000 | Jansen |
| 6,168,614 B1 | 1/2001 | Andersen et al. |
| 6,251,093 B1 | 6/2001 | Valley et al. |
| 6,312,465 B1 | 11/2001 | Griffin et al. |
| 6,358,277 B1 | 3/2002 | Duran |
| 6,440,164 B1 | 8/2002 | DiMatteo et al. |
| 6,458,153 B1 | 10/2002 | Bailey et al. |
| 6,482,228 B1 | 11/2002 | Norred |
| 6,527,800 B1 | 3/2003 | McGuckin, Jr. et al. |
| 6,582,462 B1 | 6/2003 | Andersen et al. |
| 6,610,088 B1 | 8/2003 | Gabbay |
| 6,629,534 B1 | 10/2003 | St. Goar et al. |
| 6,652,578 B2 | 11/2003 | Bailey et al. |
| 6,676,698 B2 | 1/2004 | McGuckin, Jr. et al. |
| 6,695,878 B2 | 2/2004 | McGuckin, Jr. et al. |
| 6,712,836 B1 | 3/2004 | Berg et al. |
| 6,716,207 B2 | 4/2004 | Farnholtz |
| 6,729,356 B1 | 5/2004 | Baker et al. |
| 6,730,118 B2 | 5/2004 | Spenser et al. |
| 6,746,422 B1 | 6/2004 | Noriega et al. |
| 6,749,560 B1 | 6/2004 | Konstorum et al. |
| 6,767,362 B2 | 7/2004 | Schreck |
| 6,780,200 B2 | 8/2004 | Jansen |
| 6,790,229 B1 | 9/2004 | Berreklouw |
| 6,790,230 B2 | 9/2004 | Beyersdorf et al. |
| 6,875,231 B2 | 4/2005 | Anduiza et al. |
| 6,893,460 B2 | 5/2005 | Spenser et al. |
| 6,908,481 B2 | 6/2005 | Cribier |
| 7,018,406 B2 | 3/2006 | Seguin et al. |
| 7,186,265 B2 | 3/2007 | Sharkawy et al. |
| 7,192,440 B2 | 3/2007 | Andreas et al. |
| 7,198,646 B2 | 4/2007 | Figulla et al. |
| 7,201,772 B2 | 4/2007 | Schwammenthal et al. |
| 7,276,078 B2 | 10/2007 | Spenser et al. |
| 7,329,278 B2 | 2/2008 | Seguin et al. |
| 7,381,219 B2 | 6/2008 | Salahieh et al. |
| 7,393,360 B2 | 7/2008 | Spenser et al. |
| 7,429,269 B2 | 9/2008 | Schwammenthal et al. |
| 7,442,204 B2 | 10/2008 | Schwammenthal et al. |
| 7,445,631 B2 | 11/2008 | Salahieh et al. |
| 7,462,191 B2 | 12/2008 | Spenser et al. |
| 7,510,575 B2 | 3/2009 | Spenser et al. |
| 7,524,330 B2 | 4/2009 | Berreklouw |
| 7,553,324 B2 | 6/2009 | Andreas et al. |
| 7,585,321 B2 | 9/2009 | Cribier |
| 7,618,446 B2 | 11/2009 | Andersen et al. |
| 7,621,948 B2 | 11/2009 | Herrmann et al. |
| 7,628,805 B2 | 12/2009 | Spenser et al. |
| 7,748,389 B2 | 7/2010 | Salahieh et al. |
| 7,753,949 B2 | 7/2010 | Lamphere et al. |
| 7,803,185 B2 | 9/2010 | Gabbay |
| 7,806,919 B2 | 10/2010 | Bloom et al. |
| 7,815,673 B2 | 10/2010 | Bloom et al. |
| 7,824,443 B2 | 11/2010 | Salahieh et al. |
| 7,892,281 B2 | 2/2011 | Seguin et al. |
| 7,914,569 B2 | 3/2011 | Nguyen et al. |
| 7,947,075 B2 | 5/2011 | Goetz et al. |
| 7,959,672 B2 | 6/2011 | Salahieh et al. |
| 7,972,378 B2 | 7/2011 | Tabor et al. |
| 7,981,151 B2 | 7/2011 | Rowe |
| 7,993,392 B2 | 8/2011 | Righini et al. |
| 8,016,877 B2 | 9/2011 | Seguin et al. |
| 8,048,153 B2 | 11/2011 | Salahieh et al. |
| 8,052,750 B2 | 11/2011 | Tuval et al. |
| 8,070,800 B2 | 12/2011 | Lock et al. |
| 8,070,802 B2 | 12/2011 | Lamphere et al. |
| 8,075,615 B2 | 12/2011 | Eberhardt et al. |
| 8,080,054 B2 | 12/2011 | Rowe |
| 8,092,520 B2 | 1/2012 | Quadri |
| 8,109,996 B2 | 2/2012 | Stacchino et al. |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,157,852 B2 | 4/2012 | Bloom et al. |
| 8,182,528 B2 | 5/2012 | Salahieh et al. |
| 8,182,530 B2 | 5/2012 | Huber |
| 8,216,301 B2 | 7/2012 | Bonhoeffer et al. |
| 8,219,229 B2 | 7/2012 | Cao et al. |
| 8,220,121 B2 | 7/2012 | Hendriksen et al. |
| 8,221,493 B2 | 7/2012 | Boyle et al. |
| 8,226,710 B2 | 7/2012 | Nguyen et al. |
| 8,236,045 B2 | 8/2012 | Benichou et al. |
| 8,246,675 B2 | 8/2012 | Zegdi |
| 8,246,678 B2 | 8/2012 | Salahieh et al. |
| 8,252,051 B2 | 8/2012 | Chau et al. |
| 8,252,052 B2 | 8/2012 | Salahieh et al. |
| 8,287,584 B2 | 10/2012 | Salahieh et al. |
| 8,303,653 B2 | 11/2012 | Bonhoeffer et al. |
| 8,313,525 B2 | 11/2012 | Tuval et al. |
| 8,323,335 B2 | 12/2012 | Rowe et al. |
| 8,353,953 B2 | 1/2013 | Giannetti et al. |
| 8,403,983 B2 | 3/2013 | Quadri et al. |
| 8,414,644 B2 | 4/2013 | Quadri et al. |
| 8,414,645 B2 | 4/2013 | Dwork et al. |
| 8,444,689 B2 | 5/2013 | Zhang |
| 8,449,599 B2 | 5/2013 | Chau et al. |
| 8,454,685 B2 | 6/2013 | Hariton et al. |
| 8,460,368 B2 | 6/2013 | Taylor et al. |
| 8,470,023 B2 | 6/2013 | Eidenschink et al. |
| 8,475,521 B2 | 7/2013 | Suri et al. |
| 8,475,523 B2 | 7/2013 | Duffy |
| 8,479,380 B2 | 7/2013 | Malewicz et al. |
| 8,486,137 B2 | 7/2013 | Suri et al. |
| 8,491,650 B2 | 7/2013 | Wiemeyer et al. |
| 8,500,733 B2 | 8/2013 | Watson |
| 8,500,798 B2 | 8/2013 | Rowe et al. |
| 8,511,244 B2 | 8/2013 | Holecek et al. |
| 8,512,401 B2 | 8/2013 | Murray, III et al. |
| 8,518,096 B2 | 8/2013 | Nelson |
| 8,518,106 B2 | 8/2013 | Duffy et al. |
| 8,562,663 B2 | 10/2013 | Mearns et al. |
| 8,579,963 B2 | 11/2013 | Tabor |
| 8,579,964 B2 * | 11/2013 | Lane ................... A61F 2/2409 623/2.11 |
| 8,579,965 B2 | 11/2013 | Bonhoeffer et al. |
| 8,585,755 B2 | 11/2013 | Chau et al. |
| 8,585,756 B2 | 11/2013 | Bonhoeffer et al. |
| 8,591,570 B2 | 11/2013 | Revuelta et al. |
| 8,597,348 B2 | 12/2013 | Rowe et al. |

(56) References Cited

U.S. PATENT DOCUMENTS

| | | | |
|---|---|---|---|
| 8,617,236 B2 | 12/2013 | Paul et al. | |
| 8,640,521 B2 | 2/2014 | Righini et al. | |
| 8,647,381 B2 | 2/2014 | Essinger et al. | |
| 8,652,145 B2 | 2/2014 | Maimon et al. | |
| 8,652,201 B2 | 2/2014 | Oberti et al. | |
| 8,652,202 B2 | 2/2014 | Alon et al. | |
| 8,652,203 B2 * | 2/2014 | Quadri | A61F 2/2427 623/2.11 |
| 8,668,733 B2 | 3/2014 | Haug et al. | |
| 8,673,000 B2 | 3/2014 | Tabor et al. | |
| 8,679,174 B2 | 3/2014 | Ottma et al. | |
| 8,679,404 B2 | 3/2014 | Liburd et al. | |
| 8,685,086 B2 | 4/2014 | Navia et al. | |
| 8,721,708 B2 | 5/2014 | Seguin et al. | |
| 8,721,714 B2 | 5/2014 | Kelley | |
| 8,728,154 B2 | 5/2014 | Alkhatib | |
| 8,728,155 B2 | 5/2014 | Montorfano et al. | |
| 8,740,974 B2 | 6/2014 | Lambrecht et al. | |
| 8,740,976 B2 | 6/2014 | Tran et al. | |
| 8,747,458 B2 | 6/2014 | Tuval et al. | |
| 8,747,459 B2 | 6/2014 | Nguyen et al. | |
| 8,747,460 B2 | 6/2014 | Tuval et al. | |
| 8,758,432 B2 | 6/2014 | Solem | |
| 8,764,818 B2 | 7/2014 | Gregg | |
| 8,771,344 B2 | 7/2014 | Tran et al. | |
| 8,771,345 B2 | 7/2014 | Tuval et al. | |
| 8,771,346 B2 | 7/2014 | Tuval et al. | |
| 8,778,020 B2 | 7/2014 | Gregg et al. | |
| 8,784,337 B2 | 7/2014 | Voeller et al. | |
| 8,784,478 B2 | 7/2014 | Tuval et al. | |
| 8,784,481 B2 | 7/2014 | Alkhatib et al. | |
| 8,790,387 B2 | 7/2014 | Nguyen et al. | |
| 8,795,356 B2 * | 8/2014 | Quadri | A61F 2/2409 623/2.11 |
| 8,795,357 B2 | 8/2014 | Yohanan et al. | |
| 8,801,776 B2 | 8/2014 | House et al. | |
| 8,808,356 B2 | 8/2014 | Braido et al. | |
| 8,828,078 B2 | 9/2014 | Salahieh et al. | |
| 8,828,079 B2 | 9/2014 | Thielen et al. | |
| 8,834,564 B2 | 9/2014 | Tuval et al. | |
| 8,845,718 B2 | 9/2014 | Tuval et al. | |
| 8,858,620 B2 | 10/2014 | Salahieh et al. | |
| 8,870,948 B1 | 10/2014 | Erzberger et al. | |
| 8,870,950 B2 | 10/2014 | Hacohen | |
| 8,876,893 B2 | 11/2014 | Dwork et al. | |
| 8,876,894 B2 | 11/2014 | Tuval et al. | |
| 8,876,895 B2 | 11/2014 | Tuval et al. | |
| 8,911,455 B2 | 12/2014 | Quadri et al. | |
| 8,926,693 B2 | 1/2015 | Duffy et al. | |
| 8,926,694 B2 | 1/2015 | Costello | |
| 8,939,960 B2 | 1/2015 | Rosenman et al. | |
| 8,945,209 B2 | 2/2015 | Bonyuet et al. | |
| 8,951,299 B2 | 2/2015 | Paul et al. | |
| 8,956,404 B2 * | 2/2015 | Bortlein | A61F 2/2418 623/2.11 |
| 8,961,593 B2 | 2/2015 | Bonhoeffer et al. | |
| 8,961,595 B2 | 2/2015 | Alkhatib | |
| 8,974,524 B2 | 3/2015 | Yeung et al. | |
| 8,979,922 B2 | 3/2015 | Jayasinghe et al. | |
| 8,986,371 B2 | 3/2015 | Quill et al. | |
| 8,986,372 B2 | 3/2015 | Murry, III et al. | |
| 8,986,375 B2 | 3/2015 | Garde et al. | |
| 8,992,604 B2 | 3/2015 | Gross et al. | |
| 8,992,608 B2 | 3/2015 | Haug et al. | |
| 8,998,979 B2 | 4/2015 | Seguin et al. | |
| 8,998,980 B2 | 4/2015 | Shipley et al. | |
| 9,005,273 B2 | 4/2015 | Salahieh et al. | |
| 9,011,521 B2 | 4/2015 | Haug et al. | |
| 9,011,523 B2 | 4/2015 | Seguin | |
| 9,011,524 B2 | 4/2015 | Eberhardt | |
| 9,028,545 B2 | 5/2015 | Taylor | |
| 9,034,032 B2 | 5/2015 | McLean et al. | |
| 9,034,033 B2 | 5/2015 | McLean et al. | |
| 9,039,757 B2 | 5/2015 | McLean et al. | |
| 9,055,937 B2 | 6/2015 | Rowe et al. | |
| 9,066,801 B2 | 6/2015 | Kovalsky et al. | |
| 9,078,749 B2 | 7/2015 | Lutter et al. | |
| 9,078,751 B2 | 7/2015 | Naor | |
| 9,084,676 B2 | 7/2015 | Chau et al. | |
| 9,125,738 B2 | 9/2015 | Figulla et al. | |
| 9,138,312 B2 | 9/2015 | Tuval et al. | |
| 9,161,834 B2 | 10/2015 | Taylor et al. | |
| 9,173,737 B2 | 11/2015 | Hill et al. | |
| 9,180,004 B2 | 11/2015 | Alkhatib | |
| 9,186,249 B2 | 11/2015 | Rolando et al. | |
| 9,220,594 B2 | 12/2015 | Braido et al. | |
| 9,241,790 B2 | 1/2016 | Lane et al. | |
| 9,248,014 B2 | 2/2016 | Lane et al. | |
| 9,277,990 B2 | 3/2016 | Klima et al. | |
| 9,277,993 B2 | 3/2016 | Gamarra et al. | |
| 9,289,291 B2 | 3/2016 | Gorman, III et al. | |
| 9,289,296 B2 | 3/2016 | Braido et al. | |
| 9,295,551 B2 | 3/2016 | Straubinger et al. | |
| 9,308,087 B2 | 4/2016 | Lane et al. | |
| 9,326,815 B2 | 5/2016 | Watson | |
| 9,331,328 B2 | 5/2016 | Eberhardt et al. | |
| 9,339,382 B2 | 5/2016 | Tabor et al. | |
| 9,351,831 B2 | 5/2016 | Braido et al. | |
| 9,351,832 B2 | 5/2016 | Braido et al. | |
| 9,364,321 B2 | 6/2016 | Alkhatib et al. | |
| 9,445,897 B2 | 9/2016 | Bishop et al. | |
| 9,456,877 B2 | 10/2016 | Weitzner et al. | |
| 9,480,560 B2 | 11/2016 | Quadri et al. | |
| 9,615,921 B2 | 4/2017 | Alkhatib et al. | |
| 9,681,951 B2 * | 6/2017 | Ratz | A61F 2/2409 |
| 9,681,968 B2 | 6/2017 | Goetz et al. | |
| 9,687,343 B2 | 6/2017 | Bortlein et al. | |
| 9,700,329 B2 | 7/2017 | Metzger et al. | |
| 9,700,411 B2 | 7/2017 | Klima et al. | |
| 9,730,791 B2 * | 8/2017 | Ratz | A61F 2/2418 |
| 9,795,479 B2 | 10/2017 | Lim et al. | |
| 9,833,313 B2 | 12/2017 | Board et al. | |
| 9,861,473 B2 | 1/2018 | Lafontaine | |
| 9,861,476 B2 | 1/2018 | Salahieh et al. | |
| 9,861,477 B2 | 1/2018 | Backus et al. | |
| 9,867,698 B2 | 1/2018 | Kovalsky et al. | |
| 9,877,830 B2 | 1/2018 | Lim et al. | |
| 9,889,029 B2 | 2/2018 | Li et al. | |
| 9,895,225 B2 | 2/2018 | Rolando et al. | |
| 9,925,045 B2 | 3/2018 | Creaven et al. | |
| 10,010,414 B2 * | 7/2018 | Cooper | A61F 2/2418 |
| 10,070,954 B2 * | 9/2018 | Braido | A61F 2/2409 |
| 10,098,736 B2 * | 10/2018 | Carmi | A61F 2/2442 |
| 10,117,744 B2 * | 11/2018 | Ratz | A61F 2/2418 |
| 10,179,042 B2 * | 1/2019 | Braido | A61F 2/2418 |
| 10,321,992 B2 | 6/2019 | Quill et al. | |
| 10,350,062 B2 * | 7/2019 | Peterson | A61F 2/2409 |
| 10,376,361 B2 * | 8/2019 | Gross | A61F 2/2418 |
| 10,470,876 B2 * | 11/2019 | Gurovich | A61F 2/2418 |
| 10,485,660 B2 * | 11/2019 | Quadri | A61F 2/2415 |
| 10,575,948 B2 * | 3/2020 | Iamberger | B29C 39/10 |
| 10,583,000 B2 * | 3/2020 | Ratz | A61F 2/2418 |
| 10,583,002 B2 * | 3/2020 | Lane | A61F 2/2412 |
| 10,888,421 B2 * | 1/2021 | Hariton | A61F 2/24 |
| 11,051,934 B2 * | 7/2021 | Cooper | A61F 2/2427 |
| 11,109,964 B2 * | 9/2021 | Hacohen | A61F 2/2418 |
| 2001/0007956 A1 | 7/2001 | Letac et al. | |
| 2002/0016623 A1 | 2/2002 | Kula et al. | |
| 2002/0032481 A1 | 3/2002 | Gabbay | |
| 2002/0045929 A1 | 4/2002 | Diaz | |
| 2002/0052644 A1 | 5/2002 | Shaolian et al. | |
| 2003/0105517 A1 | 6/2003 | White et al. | |
| 2003/0120333 A1 | 6/2003 | Ouriel et al. | |
| 2003/0130729 A1 | 7/2003 | Paniagua et al. | |
| 2003/0176914 A1 | 9/2003 | Rabkin et al. | |
| 2003/0199971 A1 | 10/2003 | Tower et al. | |
| 2003/0220683 A1 | 11/2003 | Minasian et al. | |
| 2004/0117009 A1 | 6/2004 | Cali et al. | |
| 2004/0133273 A1 | 7/2004 | Cox | |
| 2004/0167605 A1 | 8/2004 | Elliott | |
| 2004/0186561 A1 | 9/2004 | McGuckin et al. | |
| 2004/0210304 A1 | 10/2004 | Seguin et al. | |
| 2004/0210307 A1 | 10/2004 | Khairkhahan | |
| 2004/0215325 A1 | 10/2004 | Penn et al. | |

(56) References Cited

U.S. PATENT DOCUMENTS

| | | |
|---|---|---|
| 2004/0225353 A1 | 11/2004 | McGuckin et al. |
| 2004/0236411 A1 | 11/2004 | Sarac et al. |
| 2005/0033398 A1 | 2/2005 | Seguin |
| 2005/0075727 A1 | 4/2005 | Wheatley |
| 2005/0090887 A1 | 4/2005 | Pryor |
| 2005/0096738 A1 | 5/2005 | Cali et al. |
| 2005/0107872 A1 | 5/2005 | Mensah et al. |
| 2005/0137682 A1 | 6/2005 | Justino |
| 2005/0137686 A1 | 6/2005 | Salahieh et al. |
| 2005/0137687 A1 | 6/2005 | Salahieh et al. |
| 2005/0137691 A1 | 6/2005 | Salahieh et al. |
| 2005/0137693 A1 | 6/2005 | Haug et al. |
| 2005/0159811 A1 | 7/2005 | Lane |
| 2005/0182486 A1 | 8/2005 | Gabbay |
| 2005/0216079 A1 | 9/2005 | MaCoviak |
| 2005/0234546 A1 | 10/2005 | Nugent et al. |
| 2005/0283231 A1 | 12/2005 | Haug et al. |
| 2006/0020327 A1 | 1/2006 | Lashinski et al. |
| 2006/0052867 A1 | 3/2006 | Revuelta et al. |
| 2006/0058872 A1 | 3/2006 | Salahieh et al. |
| 2006/0095115 A1 | 5/2006 | Bladillah et al. |
| 2006/0173537 A1 | 8/2006 | Yang et al. |
| 2006/0195183 A1 | 8/2006 | Navia et al. |
| 2006/0212110 A1 | 9/2006 | Osborne et al. |
| 2006/0241745 A1 | 10/2006 | Solem |
| 2006/0259135 A1 | 11/2006 | Navia et al. |
| 2006/0265056 A1 | 11/2006 | Nguyen et al. |
| 2006/0287717 A1 | 12/2006 | Rowe et al. |
| 2006/0293745 A1 | 12/2006 | Carpentier et al. |
| 2007/0010876 A1 | 1/2007 | Salahieh et al. |
| 2007/0043435 A1 | 2/2007 | Seguin et al. |
| 2007/0050021 A1 | 3/2007 | Johnson |
| 2007/0100432 A1 | 5/2007 | Case et al. |
| 2007/0129794 A1 | 6/2007 | Realyvasquez |
| 2007/0142906 A1 | 6/2007 | Figulla et al. |
| 2007/0213813 A1 | 9/2007 | Von Segesser et al. |
| 2007/0255394 A1 | 11/2007 | Ryan |
| 2008/0021546 A1 | 1/2008 | Patz et al. |
| 2008/0071366 A1 | 3/2008 | Tuval et al. |
| 2008/0082164 A1 | 4/2008 | Friedman |
| 2008/0082165 A1 | 4/2008 | Wilson et al. |
| 2008/0097581 A1 | 4/2008 | Shanley |
| 2008/0147179 A1 | 6/2008 | Cai et al. |
| 2008/0147183 A1 | 6/2008 | Styrc |
| 2008/0161911 A1 | 7/2008 | Revuelta et al. |
| 2008/0177381 A1 | 7/2008 | Navia et al. |
| 2008/0183273 A1 | 7/2008 | Mesana et al. |
| 2008/0208328 A1 | 8/2008 | Antocci et al. |
| 2008/0228254 A1 | 9/2008 | Ryan |
| 2009/0005863 A1 | 1/2009 | Goetz et al. |
| 2009/0138079 A1 | 5/2009 | Tuval et al. |
| 2009/0171456 A1 | 7/2009 | Kveen et al. |
| 2009/0182413 A1 | 7/2009 | Burkart et al. |
| 2009/0188964 A1 | 7/2009 | Orlov |
| 2009/0270972 A1 | 10/2009 | Lane |
| 2009/0276027 A1 | 11/2009 | Glynn |
| 2009/0276040 A1 | 11/2009 | Rowe et al. |
| 2009/0281618 A1 | 11/2009 | Hill et al. |
| 2009/0287296 A1 | 11/2009 | Manasse |
| 2009/0292350 A1 | 11/2009 | Eberhardt et al. |
| 2009/0306768 A1 | 12/2009 | Quadri |
| 2010/0049313 A1* | 2/2010 | Alon ............... A61F 2/2418 623/2.11 |
| 2010/0114305 A1 | 5/2010 | Kang et al. |
| 2010/0191326 A1 | 7/2010 | Alkhatib |
| 2010/0217382 A1 | 8/2010 | Chau et al. |
| 2010/0249894 A1 | 9/2010 | Oba et al. |
| 2010/0249911 A1 | 9/2010 | Alkhatib |
| 2010/0249923 A1 | 9/2010 | Alkhatib et al. |
| 2010/0256723 A1 | 10/2010 | Murray |
| 2010/0298931 A1 | 11/2010 | Quadri et al. |
| 2010/0305685 A1 | 12/2010 | Millwee et al. |
| 2011/0004296 A1 | 1/2011 | Lutter et al. |
| 2011/0029067 A1 | 2/2011 | McGuckin, Jr. et al. |
| 2011/0137397 A1* | 6/2011 | Chau ............... A61F 2/246 623/1.11 |
| 2011/0160836 A1 | 6/2011 | Behan |
| 2011/0208297 A1 | 8/2011 | Tuval et al. |
| 2011/0208298 A1 | 8/2011 | Tuval et al. |
| 2011/0224785 A1 | 9/2011 | Hacohen |
| 2011/0264196 A1 | 10/2011 | Savage et al. |
| 2011/0313515 A1* | 12/2011 | Quadri ............ A61F 2/2418 623/2.2 |
| 2012/0022639 A1 | 1/2012 | Hacohen et al. |
| 2012/0022640 A1* | 1/2012 | Gross ............... A61F 2/2436 623/2.11 |
| 2012/0041550 A1 | 2/2012 | Salahieh et al. |
| 2012/0059454 A1 | 3/2012 | Millwee et al. |
| 2012/0078353 A1 | 3/2012 | Quadri et al. |
| 2012/0078360 A1 | 3/2012 | Rafiee |
| 2012/0101571 A1 | 4/2012 | Thambar et al. |
| 2012/0101572 A1 | 4/2012 | Kovalsky et al. |
| 2012/0123529 A1 | 5/2012 | Levi et al. |
| 2012/0191174 A1* | 7/2012 | Vinluan ............ A61F 2/958 623/1.12 |
| 2012/0215303 A1 | 8/2012 | Quadri et al. |
| 2012/0271398 A1 | 10/2012 | Essinger et al. |
| 2012/0290062 A1 | 11/2012 | McNamara et al. |
| 2012/0310328 A1 | 12/2012 | Olson et al. |
| 2013/0006294 A1 | 1/2013 | Kashkarov et al. |
| 2013/0035759 A1 | 2/2013 | Gross et al. |
| 2013/0053950 A1 | 2/2013 | Rowe et al. |
| 2013/0131788 A1 | 5/2013 | Quadri et al. |
| 2013/0144378 A1* | 6/2013 | Quadri ............ A61F 2/2418 623/2.1 |
| 2013/0211508 A1 | 8/2013 | Lane et al. |
| 2013/0253635 A1 | 9/2013 | Straubinger et al. |
| 2013/0253642 A1 | 9/2013 | Brecker |
| 2013/0310928 A1 | 11/2013 | Morriss et al. |
| 2013/0331929 A1 | 12/2013 | Mitra et al. |
| 2013/0338766 A1 | 12/2013 | Hastings et al. |
| 2013/0345786 A1 | 12/2013 | Behan |
| 2014/0018912 A1 | 1/2014 | Delaloye et al. |
| 2014/0025163 A1 | 1/2014 | Padala et al. |
| 2014/0039611 A1 | 2/2014 | Lane et al. |
| 2014/0052237 A1 | 2/2014 | Lane et al. |
| 2014/0052242 A1 | 2/2014 | Revuelta et al. |
| 2014/0100651 A1 | 4/2014 | Kheradvar et al. |
| 2014/0100653 A1 | 4/2014 | Savage et al. |
| 2014/0142694 A1 | 5/2014 | Tabor et al. |
| 2014/0163668 A1 | 6/2014 | Rafiee |
| 2014/0172077 A1 | 6/2014 | Bruchman et al. |
| 2014/0172083 A1 | 6/2014 | Bruchman et al. |
| 2014/0194981 A1 | 7/2014 | Menk et al. |
| 2014/0207231 A1 | 7/2014 | Hacohen et al. |
| 2014/0214153 A1 | 7/2014 | Ottma et al. |
| 2014/0214154 A1 | 7/2014 | Nguyen et al. |
| 2014/0214155 A1 | 7/2014 | Kelley |
| 2014/0214160 A1 | 7/2014 | Naor |
| 2014/0222136 A1 | 8/2014 | Geist et al. |
| 2014/0222139 A1 | 8/2014 | Nguyen et al. |
| 2014/0222142 A1 | 8/2014 | Kovalsky et al. |
| 2014/0230515 A1 | 8/2014 | Tuval et al. |
| 2014/0236288 A1 | 8/2014 | Lambrecht et al. |
| 2014/0257467 A1 | 9/2014 | Lane et al. |
| 2014/0277390 A1* | 9/2014 | Ratz ............... A61F 2/2418 623/1.26 |
| 2014/0277402 A1 | 9/2014 | Essinger et al. |
| 2014/0277422 A1 | 9/2014 | Ratz et al. |
| 2014/0277427 A1 | 9/2014 | Ratz et al. |
| 2014/0296973 A1 | 10/2014 | Bergheim et al. |
| 2014/0296975 A1 | 10/2014 | Tegels et al. |
| 2014/0303719 A1 | 10/2014 | Cox et al. |
| 2014/0309728 A1 | 10/2014 | Dehdashtian et al. |
| 2014/0309732 A1 | 10/2014 | Solem |
| 2014/0324160 A1 | 10/2014 | Benichou et al. |
| 2014/0324164 A1 | 10/2014 | Gross et al. |
| 2014/0330368 A1 | 11/2014 | Gloss et al. |
| 2014/0330371 A1 | 11/2014 | Gloss et al. |
| 2014/0330372 A1 | 11/2014 | Weston et al. |
| 2014/0336754 A1 | 11/2014 | Gurskis et al. |
| 2014/0343669 A1 | 11/2014 | Lane et al. |
| 2014/0343670 A1 | 11/2014 | Bakis et al. |

(56) References Cited

U.S. PATENT DOCUMENTS

| | | |
|---|---|---|
| 2014/0343671 A1 | 11/2014 | Yohanan et al. |
| 2014/0350663 A1 | 11/2014 | Braido et al. |
| 2014/0350666 A1 | 11/2014 | Righini |
| 2014/0350668 A1 | 11/2014 | Delaloye et al. |
| 2014/0350669 A1 | 11/2014 | Gillespie et al. |
| 2014/0358223 A1 | 12/2014 | Rafiee et al. |
| 2014/0364939 A1 | 12/2014 | Deshmukh et al. |
| 2014/0364943 A1 | 12/2014 | Conklin |
| 2014/0371842 A1 | 12/2014 | Marquez et al. |
| 2014/0371844 A1 | 12/2014 | Dale et al. |
| 2014/0371845 A1 | 12/2014 | Tuval et al. |
| 2014/0371847 A1 | 12/2014 | Madrid et al. |
| 2014/0371848 A1 | 12/2014 | Murray, III et al. |
| 2014/0379067 A1 | 12/2014 | Nguyen et al. |
| 2014/0379068 A1 | 12/2014 | Thielen et al. |
| 2014/0379077 A1 | 12/2014 | Tuval et al. |
| 2015/0005863 A1 | 1/2015 | Para |
| 2015/0012085 A1 | 1/2015 | Salahieh et al. |
| 2015/0018938 A1 | 1/2015 | Von Segesser et al. |
| 2015/0018944 A1 | 1/2015 | O'Connell et al. |
| 2015/0039083 A1 | 2/2015 | Rafiee |
| 2015/0045880 A1 | 2/2015 | Hacohen |
| 2015/0127093 A1* | 5/2015 | Hosmer ............... A61F 2/2433 623/2.11 |
| 2015/0142103 A1 | 5/2015 | Vidlund |
| 2015/0148731 A1 | 5/2015 | McNamara et al. |
| 2015/0157457 A1 | 6/2015 | Hacohen |
| 2015/0157458 A1 | 6/2015 | Thambar et al. |
| 2015/0173897 A1 | 6/2015 | Raanani et al. |
| 2015/0196390 A1 | 7/2015 | Ma et al. |
| 2015/0209141 A1 | 7/2015 | Braido et al. |
| 2015/0272737 A1 | 10/2015 | Dale et al. |
| 2015/0297346 A1 | 10/2015 | Duffy et al. |
| 2015/0327994 A1 | 11/2015 | Morriss et al. |
| 2015/0328001 A1 | 11/2015 | McLean et al. |
| 2015/0335429 A1 | 11/2015 | Morriss et al. |
| 2015/0351903 A1 | 12/2015 | Morriss et al. |
| 2015/0351906 A1 | 12/2015 | Hammer et al. |
| 2015/0359629 A1 | 12/2015 | Ganesan et al. |
| 2016/0000591 A1 | 1/2016 | Lei et al. |
| 2016/0030169 A1 | 2/2016 | Shahriari |
| 2016/0030170 A1 | 2/2016 | Alkhatib et al. |
| 2016/0030171 A1 | 2/2016 | Quijano et al. |
| 2016/0038281 A1 | 2/2016 | Delaloye et al. |
| 2016/0074160 A1 | 3/2016 | Christianson et al. |
| 2016/0106537 A1 | 4/2016 | Christianson et al. |
| 2016/0113765 A1 | 4/2016 | Ganesan et al. |
| 2016/0113766 A1 | 4/2016 | Ganesan et al. |
| 2016/0113768 A1 | 4/2016 | Ganesan et al. |
| 2016/0143732 A1 | 5/2016 | Glimsdale |
| 2016/0158010 A1 | 6/2016 | Lim et al. |
| 2016/0166383 A1 | 6/2016 | Lim et al. |
| 2016/0184097 A1 | 6/2016 | Lim et al. |
| 2016/0199206 A1 | 7/2016 | Lim et al. |
| 2016/0213473 A1 | 7/2016 | Hacohen et al. |
| 2016/0235529 A1 | 8/2016 | Ma et al. |
| 2016/0279386 A1 | 9/2016 | Dale et al. |
| 2016/0310267 A1 | 10/2016 | Zeng et al. |
| 2016/0331529 A1 | 11/2016 | Marchand et al. |
| 2017/0056166 A1* | 3/2017 | Ratz ................... A61F 2/2418 |
| 2017/0056169 A1* | 3/2017 | Johnson ............... A61F 2/2436 |
| 2017/0128199 A1* | 5/2017 | Gurovich .............. A61F 2/2409 |
| 2017/0128209 A1 | 5/2017 | Morriss et al. |
| 2017/0216023 A1 | 8/2017 | Lane et al. |
| 2017/0216575 A1 | 8/2017 | Asleson et al. |
| 2017/0258614 A1 | 9/2017 | Griffin |
| 2017/0325954 A1 | 11/2017 | Perszyk |
| 2017/0348096 A1 | 12/2017 | Anderson |
| 2017/0367823 A1 | 12/2017 | Hariton et al. |
| 2018/0021129 A1* | 1/2018 | Peterson ............... A61F 2/2409 623/2.17 |
| 2018/0055636 A1 | 3/2018 | Valencia et al. |
| 2018/0085218 A1 | 3/2018 | Eidenschink |
| 2018/0110534 A1 | 4/2018 | Gavala et al. |
| 2019/0083254 A1* | 3/2019 | Hariton ................ A61F 2/2427 |
| 2019/0083263 A1 | 3/2019 | Hariton et al. |
| 2019/0167423 A1* | 6/2019 | Hariton ................ A61F 2/2418 |
| 2019/0262129 A1 | 8/2019 | Cooper et al. |
| 2020/0146814 A1* | 5/2020 | Fung .................... A61F 2/2436 |
| 2020/0179109 A1* | 6/2020 | Reimer ................. A61F 2/2418 |
| 2021/0177592 A1* | 6/2021 | Lally ................... A61F 2/2418 |
| 2021/0212825 A1* | 7/2021 | Pham ................... A61F 2/2463 |

FOREIGN PATENT DOCUMENTS

| | | |
|---|---|---|
| DE | 102006052564 B3 | 12/2007 |
| EP | 1171059 A1 | 1/2002 |
| EP | 1255510 A1 | 11/2002 |
| EP | 1259194 B1 | 11/2002 |
| EP | 1281375 A2 | 2/2003 |
| EP | 1369098 A1 | 12/2003 |
| EP | 1472996 A1 | 11/2004 |
| EP | 1734903 A1 | 12/2006 |
| EP | 1827558 A2 | 9/2007 |
| EP | 1239901 B1 | 10/2007 |
| EP | 2124826 A1 | 12/2009 |
| EP | 1935377 B1 | 3/2010 |
| EP | 2237746 A2 | 10/2010 |
| EP | 2238947 A2 | 10/2010 |
| EP | 2285317 A1 | 2/2011 |
| EP | 2308425 A1 | 4/2011 |
| EP | 2319458 A1 | 5/2011 |
| EP | 2398543 A1 | 12/2011 |
| EP | 2496182 A1 | 9/2012 |
| EP | 2566416 A1 | 3/2013 |
| EP | 2745805 A1 | 6/2014 |
| EP | 2749254 A1 | 7/2014 |
| EP | 2750630 A1 | 7/2014 |
| EP | 2777617 A1 | 9/2014 |
| EP | 2815723 A1 | 12/2014 |
| EP | 2815725 A1 | 12/2014 |
| EP | 2898858 A1 | 7/2015 |
| EP | 2967858 A2 | 1/2016 |
| EP | 2926766 B1 | 2/2016 |
| EP | 2985006 A1 | 2/2016 |
| EP | 2168536 B1 | 4/2016 |
| EP | 2262451 B1 | 5/2017 |
| EP | 3184083 A1 | 6/2017 |
| EP | 2446915 B1 | 1/2018 |
| EP | 3057541 B1 | 1/2018 |
| EP | 3037064 B1 | 3/2018 |
| EP | 3046511 B1 | 3/2018 |
| EP | 3142603 B1 | 3/2018 |
| EP | 3294220 A1 | 3/2018 |
| GB | 1264471 A | 2/1972 |
| GB | 1315844 A | 5/1973 |
| GB | 2398245 A | 8/2004 |
| JP | 2002540889 A | 12/2002 |
| JP | 2008541865 A | 11/2008 |
| WO | 9749355 A1 | 12/1997 |
| WO | 0061034 A1 | 10/2000 |
| WO | 03092554 A1 | 11/2003 |
| WO | 2004030569 A2 | 4/2004 |
| WO | 2005011534 A1 | 2/2005 |
| WO | 2006070372 A2 | 7/2006 |
| WO | 2006085225 A1 | 8/2006 |
| WO | 2006089236 A1 | 8/2006 |
| WO | 2006127765 A1 | 11/2006 |
| WO | 2007025028 A1 | 3/2007 |
| WO | 2007058857 A2 | 5/2007 |
| WO | 2007123658 A1 | 11/2007 |
| WO | 2008013915 A2 | 1/2008 |
| WO | 2008070797 A2 | 6/2008 |
| WO | 2008103722 A2 | 8/2008 |
| WO | 2008125153 A1 | 10/2008 |
| WO | 2008150529 A1 | 12/2008 |
| WO | 2009026563 A2 | 2/2009 |
| WO | 2009033469 A1 | 3/2009 |
| WO | 2009045331 A1 | 4/2009 |
| WO | 2009053497 A1 | 4/2009 |
| WO | 2009091509 A1 | 7/2009 |
| WO | 2009094500 A1 | 7/2009 |
| WO | 2009134701 A2 | 11/2009 |
| WO | 2010005524 A2 | 1/2010 |

(56) References Cited

FOREIGN PATENT DOCUMENTS

| | | |
|---|---|---|
| WO | 2010008549 A1 | 1/2010 |
| WO | 2010022138 A2 | 2/2010 |
| WO | 2010037141 A1 | 4/2010 |
| WO | 2010040009 A1 | 4/2010 |
| WO | 2010057262 A1 | 5/2010 |
| WO | 2011025945 A1 | 3/2011 |
| WO | 2011057087 A1 | 5/2011 |
| WO | 2011111047 A2 | 9/2011 |
| WO | 2011137531 A1 | 11/2011 |
| WO | 2012177942 A2 | 12/2012 |
| WO | 2013028387 A2 | 2/2013 |
| WO | 2013075215 A1 | 5/2013 |
| WO | 2013120181 A1 | 8/2013 |
| WO | 2013175468 A2 | 11/2013 |
| WO | 2013192305 A2 | 12/2013 |
| WO | 2014018432 A2 | 1/2014 |
| WO | 2014099655 A1 | 6/2014 |
| WO | 2014110019 A1 | 7/2014 |
| WO | 2014110171 A2 | 7/2014 |
| WO | 2014121042 A1 | 8/2014 |
| WO | 2014139545 A1 | 9/2014 |
| WO | 2014145338 A1 | 9/2014 |
| WO | 2014149865 A1 | 9/2014 |
| WO | 2014163706 A1 | 10/2014 |
| WO | 2014164364 A1 | 10/2014 |
| WO | 2014194178 A1 | 12/2014 |
| WO | 2014204807 A1 | 12/2014 |
| WO | 2014205064 A1 | 12/2014 |
| WO | 2014210124 A1 | 12/2014 |
| WO | 2015077274 A1 | 5/2015 |
| WO | 2015148241 A1 | 10/2015 |
| WO | 2016016899 A1 | 2/2016 |

OTHER PUBLICATIONS

Banai, Shmeul et al., The Journal of the American College of Cardiology, "Transapical Mitral Implantation of the Tiara Bioprosthesis Pre-Clinical Results," Feb. 2014, <http://interventions.onlinejacc.org/article.aspx?articleid=1831234>.

Bavaria, Joseph E. M.D. et al.: "Transcatheter Mitral Valve Implantation: The Future Gold Standard for MR?," Applicant requests the Examiner to consider this reference to be prior art as of Dec. 2010.

Bavaria, Joseph E. M.D.: "CardiAQ Valve Technologies: Transcatheter Mitral Valve Implantation," Sep. 21, 2009.

Berreklouw, Eric, PhD, et al., "Sutureless Mitral Valve Replacement With Bioprostheses and Nitinol Attachment Rings: Feasibility In Acute Pig Experiments," The Journal of Thoracic and Cardiovascular Surgery, vol. 142, No. 2, Aug. 2011 in 7 pages, Applicant believes this may have been available online as early as Feb. 7, 2011.

BioSpace, "CardiAQ Valve Technologies (CVT) Reports Cardiovascular Medicine Milestone: First-In-Humannonsurgical Percutaneous Implantation of a Bioprosthetic Mitral Heart Valve," Jun. 14, 2012, p. 1, http://www.biospace.com/News/cardiaq-valve-technologies-cvt-reports/263900.

BioSpace, "CardiAQ Valve Technologies (CVT) Reports First-In-Human Percutaneous Transfemoral, Transseptal Implantation With Its Second Generation Transcatheter Bioprosthetic Mitral Heart Valve," Jun. 23, 2015, p. 1, http://www.biospace.com/News/cardiaq-valve-technologies-cvt-reports-first-in/382370.

Boudjemline, Younes, et al., "Steps Toward the Percutaneous Replacement of Atrioventricular Valves," JACC, vol. 16, No. 2, Jul. 19, 2005:360-5.

"CardiAQTM Valve Technologies reports Successful First-in-Human Trans-Apical implantation of its Second Generation Transcatheter Mitral Valve," CardiAQ Valve Technologies Press Release, May 20, 2014.

CardiAQ Valve Technologies, "Innovations in Heart Valve Therapy," In3 San Francisco, Jun. 18, 2008, PowerPoint presentation in 19 slides.

Chiam, Paul T.L., et al., "Percutaneous Transcatheter Aortic Valve Implantation: Assessing Results, Judging Outcomes, and Planning Trials," JACC: Cardiovascular Interventions, The American College of Cardiology Foundation, vol. 1, No. 4, Aug. 2008:341-50.

"Company Overview," at TVT on Jun. 25, 2009.

Condado, Jose Antonio, et al., "Percutaneous Treatment of Heart Valves," Rev Esp Cardio. 2006;59(12):1225-31, Applicant believes this may have been available as early as Dec. 2006.

Engager System, Precise Valve Positioning, Transcatheter Aortic Valve Implantation System, Transcatheter Aortic Valve Replacement—TAVR I Medtronic Engager, http://www.medtronic-engager.com/home/transcatheter-aortic-valve-repl., 2014 Medtronic, Inc. in 2 pages. Applicant believes this may have been available online as early as Aug. 25, 2013.

Fornell, Dave, "Transcatheter Mitral Valve replacement Devices in Development," Diagnostic and Interventional Cardiology, Dec. 30, 2014, p. 3, <http://www.dicardiology.com/article/transcatheter-milral-valve-replacement-devices-development>.

Fanning, Jonathon P., et al., "Transcatheter Aortic Valve Implantation (TAVI): Valve Design And Evolution," International Journal of Cardiology 168 (2013) 1822-1831, Applicant believes this may have been available as early as Oct. 3, 2013.

Feldman, Ted, MD. "Prospects for Percutaneous Valve Therapies," Circulation 2007; 116:2866-2877. Applicant believes that this may be available as early as Dec. 11, 2007.

Fitzgerald, Peter J. M.D., "Tomorrow's Technology: Percutaneous Mitral Valve Replacement, Chordal Shortening, and Beyond," Transcatheter Valve Therapies (TVT) Conference. Seattle, WA. Applicant believes this may have been available as early as Jun. 7, 2010.

Grube, E. et al., "Percutaneous aortic valve replacement for severe aortic stenosis in high-risk patients using the second- and current third-generation self-expanding CoreValve prosthesis: device success and 30-day clinical outcome." J Am Coll Cardiol. Jul. 3, 2007;50(1):69-76. Epub Jun. 6, 2007.

Horvath et al.: "Transapical Aortic Valve Replacement under Real-time Magnetic Resonance Imaging Guidance: Experimental Results with Balloon-Expandable and Self-Expanding Stents," http://www.ncbi.nlm.nih.gov/pmc/articles/PMC3038190/. Jun. 2011.

Karimi, Houshang, et al., "Percutaneous Valve Therapies," SIS 2007 Yearbook, Chapter 11, pp. 1-11.

Kronemyer, Bob, "CardiAQ Valve Technologies: Percutaneous Mitral Valve Replacement," Start Up—Windhover Review of Emerging Medical Ventures, vol. 14, Issue No. 6, Jun. 2009, pp. 48-49.

Leon, Martin B., et al., "Transcatheter Aortic Valve Replacement in Patients with Critical Aortic Stenosis: Rationale, Device Descriptions, Early Clinical Experiences, and Perspectives," Semin. Thorac. Cardiovasc. Surg. 18:165-174, 2006 in 10 pages, Applicant believes this may have been available as early as the Summer of 2006.

Lutter, Georg, et al., "Off-Pump Transapical Mitral Valve Replacement," European Journal of Cardio-thoracic Surgery 36 (2009) 124-128, Applicant believes this may have been available as early as Apr. 25, 2009.

Ma, Liang, et al., "'Double-Crowned Valved Stents For Off-Pump Mitral Valve Replacement," European Journal of Cardio-thoracic Surgery 28 (2005) 194-199, Applicant believes this may have been available as early as Aug. 2005.

Mack, Michael, M.D., "Antegrade Transcatheter Mitral valve Implantation: A Short-term Experience in Swine Model," Applicant believes this may have been presented on May 2011 at TVT.

Mack, Michael M.D., "Advantages and Limitations of Surgical Mitral Valve Replacement; Lessons for the Transcatheter Approach," Applicant believes this may have been available as early as Jun. 7, 2010. Applicant believes this may have been presented at the Texas Cardiovascular Innovative Ventures (TCIV) Conference in Dallas, TX on Dec. 8, 2010.

Mack, Michael, M.D., "Antegrade Transcatheter Mitral valve Implantation: On-Going Experience in Swine Model," Applicant believes this may have been presented on Nov. 2011 at TCT.

Masson, Jean-Bernard, et al., "Percutaneous Treatment of Mitral Regurgitation," Circulation: Cardiovascular Interventions, 2:140-146, Applicant believes this may have been available as early as Apr. 14, 2009.

(56) References Cited

OTHER PUBLICATIONS

Neovasc corporate presentation, Oct. 2009, available at http://www.neovasc.com/investors/documents/Neovasc-Corporate-Presentation-October-2009.pdf.
NJ350: Vote for Your Favorite New Jersey Innovations, Jun. 27, 2014, http://www.kilmerhouse.com/2014/06/nj350-vote-for-your-favorite-new-jersey-innovations/.
Ostrovsky, Gene, "Transcatheter Mitral Valve Implantation Technology from CardiAQ," medGadget, Jan. 15, 2010, available at: http://www.medgadget.com/2010/01/transcatheter_mitral_valve_implantation_technology_from_cardiaq.html.
Piazza, Nicoló, MD, et al., "Anatomy of the Aortic Valvar Complex and Its Implications for Transcatheter Implantation of the Aortic Valve," Contemporary Reviews in Interventional Cardiology, Circ. Cardiovasc. Intervent., 2008;1:74-81, Applicant believes this may have been available as early as Aug. 2008.
Pluth, James R., M.D., et al., "Aortic and Mitral Valve Replacement with Cloth-Covered Braunwald-Cutter Prosthesis A Three-Year Follow-up," The Annals Of Thoracic Surgery, vol. 20, No. 3, Sep. 1975, pp. 239-248.
Preston-Maher, Georgia L., et al., "A Technical Review of Minimally Invasive Mitral Valve Replacements," Cardiovascular Engineering and Technology, vol. 6, No. 2, Jun. 2015, pp. 174-184. Applicant believes this may have been available as early as Nov. 25, 2014.
Quadri, Arshad M.D., "Transcatheter Mitral Valve Implantation (TMVI) (An Acute In Vivo Study)," Applicant believes this may have been presented on Sep. 22, 2010 at TCT.
Ratz, J. Brent et al., "Any experiences making an expandable stent frame?" Arch-Pub.com, Architecture Forums Modeling, Multiple forum postings from Feb. 3, 2009 to Feb. 4, 2009, http://www.arch-pub.com.
Ratz, J. Brent, "In3 Company Overview," Jun. 24, 2009.
Ratz, J. Brent, "LSI EMT Spotlight," May 15, 2009.
Ruiz, Carlos E., "Overview of Novel Transcatheter Valve Technologies," Applicant believes this may have been presented on May 27, 2010 at EuroPCR.
Seidel, Wolfgang, et al., "A Mitral Valve Prosthesis and a Study of Thrombosis on Heart Valves in Dogs," JSR—vol. II, No. 3—May 1962, submitted for publication Oct. 9, 1961.
Sondergaard, Lars, "CardiAQ TMVR FIH—Generation 2," Applicants believe this may have been presented in 2014 at the TVT symposium.
Sondergaard, Lars, et al., "Transcatheter Mitral Valve Implantation: CardiAQ™," Applicant believes this may have Seen presented at EuroPCR 2013.
Sondergaard, Lars, et al., "Transcatheter Mitral Valve Implantation: CardiAQ™," Applicant believes this may have Seen presented at TCT 2013.
Spillner, J. et al., "New Sutureless 'Atrial-Mitral-Valve Prosthesis' For Minimally Invasive Mitral Valve Therapy," Textile Research Journal, 2010, in 7 pages, Applicant believes this may have been available as early as Aug. 9, 2010.
Taramasso et al.: "New devices for TAVI: technologies and initial clinical experiences" http://www.nature.com/nrcardio/journal/v11/n3/full/nrcardio.2013.221.html?message-global=remove#access. Jan. 21, 2014.
Treede et al.: "Transapical transcatheter aortic valve implantation using the JenaValve™ system: acute and 30-day results of the multicentre CE-mark study." http://ejcts.oxfordjournals.org/content/41/6/e131.long. Apr. 16, 2012.
"Update," Applicant believes this may have been presented on Jun. 6, 2010 at TVT.
Van Mieghem, et al., "Anatomy of the Mitral Valvular Complex and Its Implications for Transcatheter Interventions for Mitral Regurgitation," J. Am. Coll. Cardiol., 56:617-626 (Aug. 17, 2010).
Vu, Duc-Thang, et al., "Novel Sutureless Mitral Valve Implantation Method Involving A Bayonet Insertion And Release Mechanism: A Proof Of Concept Study In Pigs," The Journal of Thoracic and Cardiovascular Surgery, vol. 143, No, 4, 985-988, Apr. 2012, Applicant believes this may have been available online as early as Feb. 13, 2012.
Wayback Machine, Cleveland Clinic Lerner Research Institute, Transcatheter Mitral Stent/Valve Prosthetic, https://web.archive.org/web/20130831094624/http://mds.clevelandclinic.org/Portfolio.aspx?n=331, indicated as archived on Aug. 31, 2013.
Webb, John G., et al., "Transcatheter Aortic Valve Implantation: The Evolution Of Prostheses, Delivery Systems And Approaches," Archives of Cardiovascular Disease (2012) 105,153-159. Applicant believes this may have been available as early as Mar. 16, 2012.

* cited by examiner

PROSTHESIS FOR ATRAUMATICALLY GRASPING INTRALUMENAL TISSUE AND METHODS OF DELIVERY

CROSS-REFERENCE TO RELATED APPLICATIONS

This application is a continuation of U.S. patent application Ser. No. 15/947,168, filed Apr. 6, 2018, entitled "PROSTHESIS FOR ATRAUMATICALLY GRASPING INTRALUMENAL TISSUE AND METHODS OF DELIVERY", which is a continuation of U.S. patent application Ser. No. 14/197,690, filed Mar. 5, 2014, entitled "PROSTHESIS FOR ATRAUMATICALLY GRASPING INTRALUMENAL TISSUE AND METHODS OF DELIVERY", which claims the benefit of priority to U.S. Provisional Appl. No. 61/782,707, filed Mar. 14, 2013, entitled "PROSTHESIS FOR ATRAUMATICALLY GRASPING INTRALUMENAL TISSUE AND METHODS OF DELIVERY". The entire contents of the above application(s) is/are hereby incorporated by reference and made a part of this specification. Any and all priority claims identified in the Application Data Sheet, or any correction thereto, are hereby incorporated by reference under 37 CFR 1.57.

BACKGROUND OF THE INVENTION

Field of the Invention

Certain embodiments disclosed herein relate generally to prostheses for implantation within a lumen or body cavity. In particular, certain embodiments relate to expandable prostheses such as replacement heart valves, such as for the mitral valve, that are configured to atraumatically grasp intralumenal tissue.

Description of the Related Art

Human heart valves, which include the aortic, pulmonary, mitral and tricuspid valves, function essentially as one-way valves operating in synchronization with the pumping heart. The valves allow blood to flow downstream, but block blood from flowing upstream. Diseased heart valves exhibit impairments such as narrowing of the valve or regurgitation, which inhibit the valves' ability to control blood flow. Such impairments reduce the heart's blood-pumping efficiency and can be a debilitating and life threatening condition. For example, valve insufficiency can lead to conditions such as heart hypertrophy and dilation of the ventricle. Thus, extensive efforts have been made to develop methods and apparatuses to repair or replace impaired heart valves.

Prostheses exist to correct problems associated with impaired heart valves. For example, mechanical and tissue-based heart valve prostheses can be used to replace impaired native heart valves. More recently, substantial effort has been dedicated to developing replacement heart valves, particularly tissue-based replacement heart valves that can be delivered with less trauma to the patient than through open heart surgery. Replacement valves are being designed to be delivered through minimally invasive procedures and even percutaneous procedures. Such replacement valves often include a tissue-based valve body that is connected to an expandable frame that is then delivered to the native valve's annulus.

Development of prostheses including but not limited to replacement heart valves that can be compacted for delivery and then controllably expanded for controlled placement has proven to be particularly challenging. An additional challenge relates to the ability of such prostheses to be secured relative to intralumenal tissue, e.g., tissue within any body lumen or cavity, in an atraumatic manner. Further challenges arise when trying to controllably deliver and secure such prostheses in a location such as at a native mitral valve.

SUMMARY OF THE INVENTION

Embodiments of the present disclosure are directed to a prosthesis, such as but not limited to a replacement heart valve. Further embodiments are directed to methods of delivering a prosthesis into a body cavity and/or securing a prosthesis to intralumenal tissue. In some embodiments, a replacement heart valve and methods for delivering a replacement heart valve to a native heart valve, such as a mitral valve, are provided.

In some embodiments a prosthesis can comprise an expandable frame, a plurality of distal anchors and a plurality of proximal anchors. The anchors can extend outwardly from the frame. The frame can be configured to radially expand and contract for deployment within the body cavity. In some embodiments, when the frame is in an expanded configuration, the frame can have a larger cross-sectional dimension in a middle portion of the frame and a smaller cross-sectional dimension in a proximal portion and a distal portion of the frame, wherein the middle portion is between the proximal and distal portions. In some embodiments, at least some of the anchors comprise a loop that forms an atraumatic end of a corresponding anchor.

In some embodiments, a prosthesis can be configured to atraumatically grasp intralumenal tissue when deployed within a body cavity. The prosthesis can comprise an expandable frame comprising a proximal end and a distal end and having a longitudinal axis extending between the proximal end and the distal end. The frame can be configured to radially expand and contract for deployment within the body cavity, wherein when the frame is in an expanded configuration, the frame has a larger cross-sectional dimension in a middle portion of the frame and a smaller cross-sectional dimension in a proximal portion and a distal portion of the frame, wherein the middle portion is between the proximal and distal portions. The prosthesis can also include a plurality of generally distally extending anchors extending from the proximal portion of the frame and configured so that when the frame is in an expanded configuration each distally extending anchor has an end positioned radially outward from the middle portion of the frame, and a plurality of generally proximally extending anchors extending from the distal portion of the frame and configured so that when the frame is in an expanded configuration each proximally extending anchor has an end positioned radially outward form the middle portion of the frame and axially spaced from the ends of the distally extending anchors. At least some of the anchors can comprise a loop that forms an atraumatic end of the anchor The frame can be configured such that radial expansion of the frame causes the ends of the plurality of distally extending anchors and the ends of the plurality of proximally extending anchors to draw closer together.

A prosthesis according to certain embodiments can be configured to atraumatically grasp intralumenal tissue when deployed within a body cavity. The prosthesis can comprise an expandable frame, a plurality of proximal anchors each connected to the frame so that when the frame is in an expanded configuration an end of each proximal anchor is positioned radially outward from the frame and extends generally distally, and a plurality of distal anchors each connected to the frame so that when the frame is in an expanded configuration an end of each distal anchor is positioned radially outward from the frame and extends generally proximally, wherein the ends of the distal anchors are axially spaced from the ends of the proximal anchors when the frame is in an expanded configuration. In some embodiments, at least some of the anchors can comprise a looped end.

Alternatively, or in addition, in some embodiments, at least some of the anchors can comprise a loop. Each loop of these later embodiments can comprise first through fourth segments and an arcuate segment. The first and second segments can both extend in a first generally axial direction away from the frame. The third and fourth segments can extend radially outward from the frame in a second direction generally opposite the first direction, the third segment connected to the first segment and the fourth segment connected to the second segment. The arcuate segment can connect the third segment and the fourth segment that forms an atraumatic end of a corresponding anchor. In some embodiments, the frame is configured such that radial expansion of the frame causes the ends of the plurality of proximal anchors and the ends of the plurality of distal anchors to draw closer together.

In some embodiments, a prosthesis can be configured to atraumatically grasp intralumenal tissue when deployed within a body cavity. The prosthesis can comprise an expandable frame, a plurality of proximal anchors, and a plurality of distal anchors. The expandable frame can comprise a proximal end and a distal end and having a longitudinal axis extending between the proximal end and the distal end, the frame configured to radially expand and contract for deployment within the body cavity. The plurality of proximal anchors can each connect to the frame so that when the frame is in an expanded configuration an end of each proximal anchor is positioned radially outward from the frame and extends generally distally. The plurality of distal anchors can each connect to the frame so that when the frame is in an expanded configuration an end of each distal anchor is positioned radially outward from the frame and extends generally proximally, wherein the ends of the distal anchors are axially spaced from the ends of the proximal anchors when the frame is in an expanded configuration. At least some of the anchors can comprise a loop. Each of the anchors that comprises a loop can comprise at least a first segment extending in a first generally axial direction away from the frame, and a second segment and a third segment extending radially outward from the frame in a second direction generally opposite the first direction and coming together in an atraumatic end. The frame can be configured such that radial expansion of the frame causes the ends of the plurality of proximal anchors and the ends of the plurality of distal anchors to draw closer together.

According to some embodiments a prosthesis can be configured to atraumatically grasp intralumenal tissue when deployed within a body cavity. The prosthesis can comprise an expandable frame comprising a proximal end and a distal end and having a longitudinal axis extending between the proximal end and the distal end, the frame configured to radially expand and contract for deployment within the body cavity, a plurality of proximal anchors each connected to the frame so that when the frame is in an expanded configuration an end of each proximal anchor is positioned radially outward from the frame and extends generally distally, and a plurality of distal anchors each connected to the frame so that when the frame is in an expanded configuration an end of each distal anchor is positioned radially outward from the frame and extends generally proximally, wherein the ends of the distal anchors are axially spaced from the ends of the proximal anchors when the frame is in an expanded configuration. At least some of the anchors can comprise a loop and each loop can comprise first through fourth segments and an arcuate segment. The first and second segments can both extend in a first generally axial direction away from the frame. The third and fourth segments can extend radially outward from the frame in a second direction generally opposite the first direction, the third segment connected to the first segment and the fourth segment connected to the second segment. The arcuate segment can connect the third segment and the fourth segment that forms an atraumatic end of a corresponding anchor. The frame can be configured such that radial expansion of the frame causes the ends of the plurality of proximal anchors and the ends of the plurality of distal anchors to draw closer together.

Methods of delivering a prosthesis and/or securing the prosthesis to intralumenal tissue are also provided. In one embodiment, a method of delivering a replacement valve to a native mitral valve can comprise one or more of the following steps. Delivering a replacement valve mounted on a delivery device to the native mitral valve annulus while the replacement valve is in a radially compacted state, the replacement valve comprising a radially expandable frame comprising a proximal end, a distal end, a plurality of distal anchors extending generally proximally from the frame, and a plurality of proximal anchors extending generally distally from the frame. Positioning the replacement valve so that ends of the distal anchors are on a ventricular side of the native leaflets beyond a location where chordae tendineae connect to free ends of the native leaflets. Releasing at least a portion of the replacement valve from the delivery device to thereby expand the distal anchors radially outwardly to a first radial dimension. Moving the ends of the distal anchors toward the ventricular side of the native valve annulus with the distal anchors extending between at least some of the chordae tendineae to provide tension on the chordae tendineae. Further releasing the replacement valve from the delivery device to thereby expand the proximal anchors radially outwardly to a second radial dimension greater than the first radial dimension, wherein the proximal anchors upon further release of the replacement valve from the delivery device move into engagement with tissue on an atrial side of the native valve annulus while the distal anchors provide tension on the chordae tendineae.

BRIEF DESCRIPTION OF THE DRAWINGS

These and other features, aspects and advantages are described below with reference to the drawings, which are intended to illustrate but not to limit the invention. In the drawings, like reference characters denote corresponding features consistently throughout similar embodiments.

DETAILED DESCRIPTION OF THE PREFERRED EMBODIMENTS

The present specification and drawings provide aspects and features of the disclosure in the context of several embodiments of prostheses, replacement heart valves, delivery devices and methods that are configured for use in the vasculature of a patient, such as for replacement of natural heart valves in a patient. These embodiments may be discussed in connection with replacing specific valves such as the patient's aortic or mitral valve. However, it is to be understood that the features and concepts discussed herein can be applied to products other than heart valve implants. For example, the controlled positioning, deployment, and securing features described herein can be applied to medical implants, for example other types of expandable prostheses, for use elsewhere in the body, such as within a vein, or the like. In addition, particular features of a valve, delivery device, etc. should not be taken as limiting, and features of any one embodiment discussed herein can be combined with features of other embodiments as desired and when appropriate.

Figure 1A:
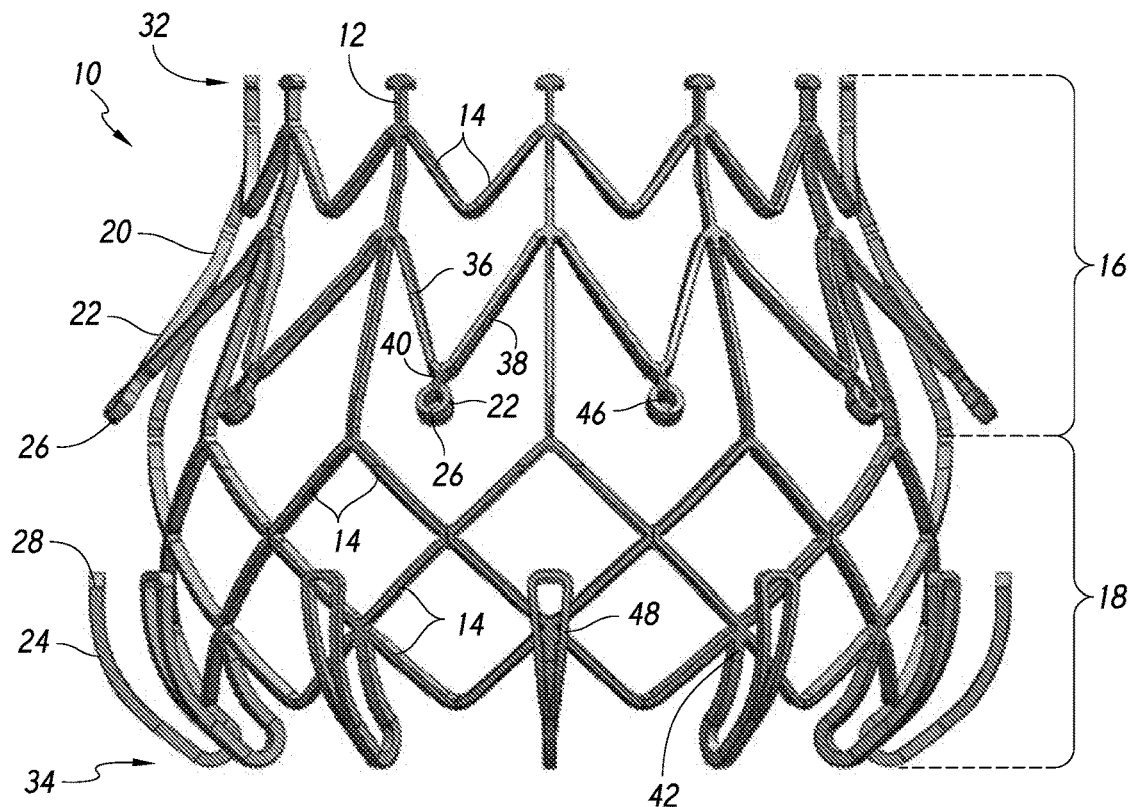
FIG. 1A is a side view of an embodiment of a prosthesis.

With initial reference to FIG. 1A, an embodiment of a prosthesis 10 is shown. The illustrated prosthesis 10 includes a frame 20 that may be self-expanding or balloon expandable. The prosthesis may further include a replacement valve that can be designed to replace a damaged or diseased native heart valve such as a mitral valve. The replacement valve is not shown in this embodiment as to more clearly illustrate features of the frame 20, though it will be understood that a replacement valve is not required as part of the prosthesis. In addition, it will be understood that only a front portion of the frame 20 is shown for further ease of illustration.

Figure 1B:
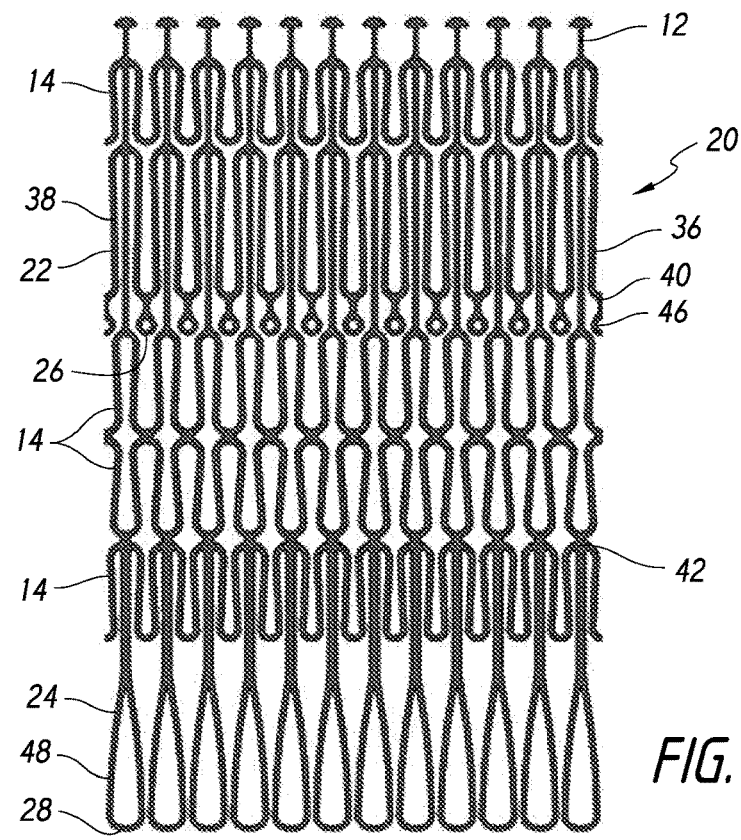
FIG. 1B is a flat pattern view of the prosthesis of FIG. 1A.

The frame 20 can be made of many different materials, but is preferably made from metal. In some embodiments, the frame 20 can be made from a shape memory material, such as nitinol. A wire frame or a metal tube can be used to make the frame. The wire frame of a metal tube can be cut or etched to remove all but the desired metal skeleton. In some embodiments a metal tube is laser cut in a repeating pattern to form the frame. FIG. 1B illustrates the flat cut pattern of the frame shown in FIG. 1A. The flat pattern can be cut from a metal tube and then the tube can be bent and expanded to the shape shown in FIG. 1A. The frame 20 can further be expanded and/or compressed and/or otherwise worked to have the desired shape or shapes, such as for introduction and implantation.

As shown, the frame when in an expanded configuration, such as in a fully expanded configuration, has a bulbous or slightly bulbous shape, with a middle portion being larger than the proximal 32 and distal 34 ends. In some embodiments, the inside diameter of the both ends can be the same, or it can be bigger on one end than the other, while still having a middle portion larger than both the proximal and distal ends. In some embodiments, the effective diameter of the distal frame end is smaller than the effective diameter of the middle portion. The bulbous shape of the frame can advantageously allow the frame to engage a native valve annulus or other body cavity, while spacing the inlet and outlet from the heart or vessel wall. This can help reduce undesired contact between the prosthesis and the heart or vessel, such as the ventricular wall of the heart. In other embodiments, the frame may not have a bulbous portion, and can have substantially the same outer dimension along its entire length, or it may have one end larger than the other end. The prosthesis 10 and frame 20 may be similar to the replacement heart valves and associated frames disclosed in U.S. Pat. No. 8,403,983 and U.S. Publication Nos. 2010/0298931, 2011/0313515 and 2012/0078353 the entireties of each of which are hereby incorporated by reference and made a part of this specification. This is inclusive of the entire disclosure and is not in any way limited to the disclosure of the replacement heart valves and associated frames.

A number of struts collectively make up the frame 20. FIG. 1 illustrates the frame in an expanded configuration with a number of longitudinal struts 12 and undulating struts 14, with cells defined by the open spaces between the struts. The longitudinal struts may be arranged so that they are parallel or generally or substantially parallel to a longitudinal axis of the frame. The longitudinal axis of the frame may be defined as the central axis that extends through the center of the frame between the proximal 32 and distal 34 ends. Any number of configurations of struts can be used, such as the rings of undulating struts shown forming chevrons and diamonds, but also ovals, curves, and various other shapes. The illustrated embodiment includes two rings, or rows of chevrons shown in portion 16 and two rows of diamond-shaped cells shown in portion 18.

The frame 20 has a non-foreshortening portion 16 and a foreshortening portion 18. These portions can be defined by the frame 20 and the positioning of various types of struts along the frame 20. In FIG. 1 it can be seen that the longitudinal struts 12 span the length of the non-foreshortening portion 16, while undulating struts 14 form the foreshortening portion 18. When the frame is radially collapsed or compacted, the struts 14 become more parallel with respect to the longitudinal axis of the frame, causing an outer diameter of the frame to decrease and the longitudinal length of the frame to increase in the foreshortening portion 18. As the frame moves from a compacted position to an expanded position, the longitudinal length of the frame can decrease in the foreshortening portion 18. But, the frame length does not substantially change length in the non-foreshortening portion 16.

Foreshortening of the frame 20 can be used to engage and secure the prosthesis to intralumenal tissue in a body cavity, for example tissue at or adjacent a native valve, such as a native valve annulus and/or leaflets. Opposing anchors 22, 24 can be constructed on the frame 20 so that portions of the anchors, such as tips or ends 26, 28, move closer together as the frame foreshortens. As one example, this can allow the anchors 22, 24 to grasp tissue on opposite sides of the native mitral annulus to thereby secure the prosthesis at the mitral valve.

The anchors 22, 24 and anchor tips 26, 28 can be located anywhere along the frame 20 just so long as at least one of the anchors is either connected to the foreshortening portion 18 or the foreshortening portion is positioned between the anchors so that a portion of the anchors will be move closer together with expansion of the frame. As shown, the anchors 24 are connected to the foreshortening portion 18. The foreshortening portion can also be positioned anywhere along the frame, though it is shown towards the distal end 34. In some embodiments, both of the anchor tips 26, 28 are located in the foreshortening portion 18. In some embodiments, the foreshortening portion 18 may extend the entire length of the frame, such that there is no non-foreshortening portion 16.

Preferably, each of the anchors 22, 24 is positioned or extends generally radially outwardly from the frame 20 so that the anchor tips 26, 28 are generally spaced away or radially outward from the rest of the frame 20. For example, the anchor tips may be located radially outward from the middle portion of the frame, with the tips 26 and 28 being axially spaced from one another. In some embodiments, all or part of the structure connected to the anchor tip and extending radially from the frame, including one or more rings and/or struts, can be considered part of the anchor. The anchors can include a base located on the anchor on a side opposite the tip. The base can be for example where the anchor begins to extend from or away from the frame 20.

For example, proximal anchors 22 are shown having first 36 and second 38 struts forming a chevron and connected to longitudinal struts 12 at a base of the anchor. The first and second struts of the anchor 22 are bent at the base so that the anchor 22 extends radially outwardly from the frame as it extends generally distally towards the tip 26. The first and second struts can be connected to each other at a radially outward location to form an outwardly extending loop, and in some embodiments, the first and second struts can be joined at a third strut 40 that continues to extend outwardly and/or generally distally. Here the third strut 40 is a short strut. The anchor also includes an eyelet 46. As illustrated, the eyelet is located at the distal end 26, though the eyelet can be positioned in other locations along the anchor 22. The tips 26 of the proximal anchors may extend distally and be parallel or substantially parallel with the longitudinal axis of the frame, or as illustrated in FIG. 1A, the tips 26 may extend generally distally but still radially outwardly inclined or at an acute angle relative to the longitudinal axis of the frame.

As another example, the distal anchors 24 are shown having looped ends 48. The looped ends can be larger near the tip to form a type of elongated teardrop. In addition, the tips 28 may be substantially flat. The looped end may assist the frame in not getting caught up on structures at or near the treatment location. For example, each loop can be configured so that when the frame is deployed in-situ and expands, the movement of each loop from a delivered position to a deployed position can avoids getting caught on the papillary muscles.

Each distal anchor 24 is connected to the frame at a base 42. As illustrated in FIG. 1A, the base of the distal anchor may be at a location where the corners of adjacent cells meet, such that the base is proximal to the distal end 34 of the frame. In other embodiments, the base of the distal anchor may be at a distal most corner of a cell, which corresponds to a distal most point on the frame The distal anchors as illustrated extend from the base 42 generally distally before bending back around in an arcuate segment where the distal anchor extends generally proximally and radially outwardly from the frame. As shown, the anchors 24 may also generally distally and radially inwardly with respect to the frame such that the distal most point on the prosthesis has a smaller inside diameter than where the base 42 connects to the frame. The inside diameter at the distal most can be the same or substantially the same as the inside diameter of the proximal end, or may be smaller. The anchor as illustrated is bent around about 180 degrees so that the tip 28 extends in the opposite, proximal direction, which may be parallel or substantially parallel to the longitudinal axis of the frame. For example, in FIG. 1A it can be seen that the distal anchors 24 are bent further inward such that the ends of the anchors point proximally and are generally parallel with the longitudinal axis of the frame. Alternatively, the tip 28 may extend generally proximally but still extend radially outwardly inclined or at an acute angle relative to the longitudinal axis of the frame It will be understood that the anchors can have various other configurations, including the various embodiments that follow. In some embodiments, each of the anchors can extend radially outwardly from the frame at an anchor base and terminate at an anchor tip. The anchors can be connected to the frame at one of many different locations including apices, junctions, other parts of struts, etc. The anchors can comprise first, second, third, or more spaced apart bending stages along the length of each anchor. The anchors can also extend either distally or proximally before and/or after one or more of the bending stages. A portion of the anchor may extend with the frame before or after any bending stages.

In the illustrated embodiment of FIG. 1A-B there are twelve distal anchors and twelve proximal anchors. In some embodiments there may be 6 anchors on one side and 12 on the other. Some embodiments may include different numbers of anchors. In addition, the distal and proximal anchors may be aligned so the tips point generally towards each other, or they may be spaced so that the tips point between two tips on the opposite side, as is illustrated in FIGS. 1A-B.

The anchor tips 26 and 28 as described above advantageously provide atraumatic surfaces that may be used to grasp intralumenal tissue without causing unnecessary or undesired trauma to tissue. For example, the proximal anchors tips 26 and distal anchor tips 28 may form flat, substantially flat, curved or other non-sharp surfaces to allow the tips to engage and/or grasp tissue, without necessarily piercing or puncturing through tissue.

Figure 2A:
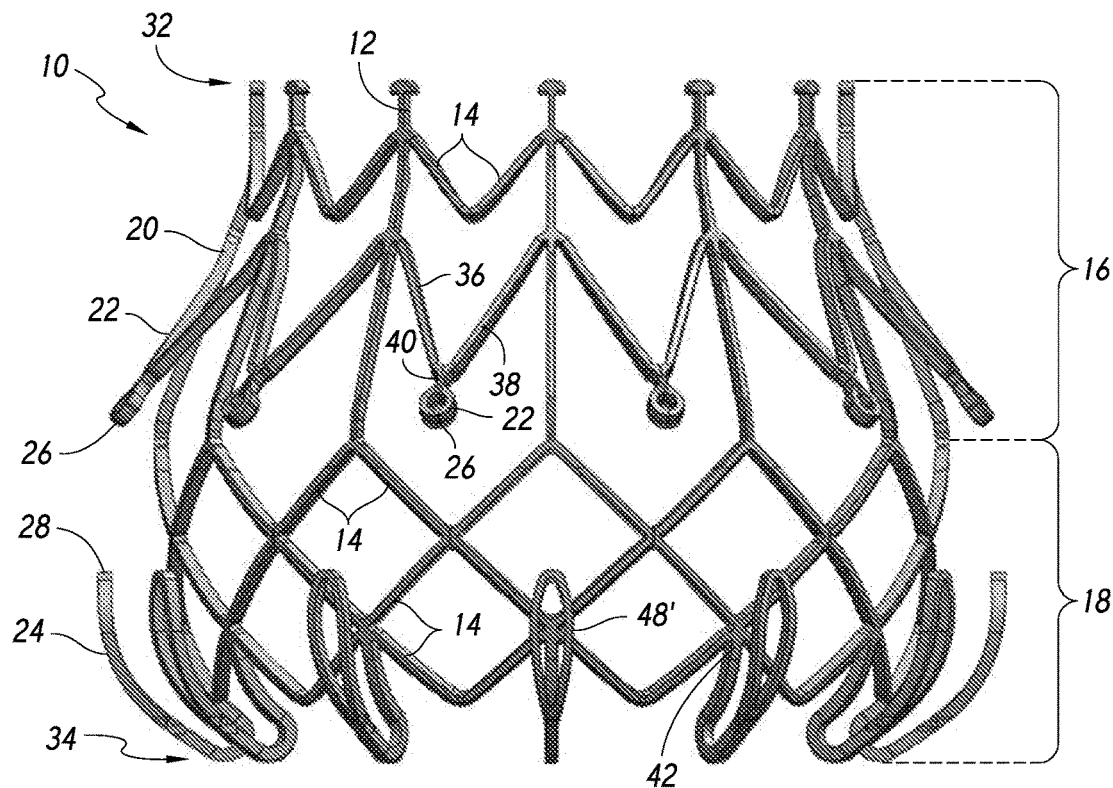
FIG. 2A is a side view of an embodiment of a prosthesis.
Figure 2B:
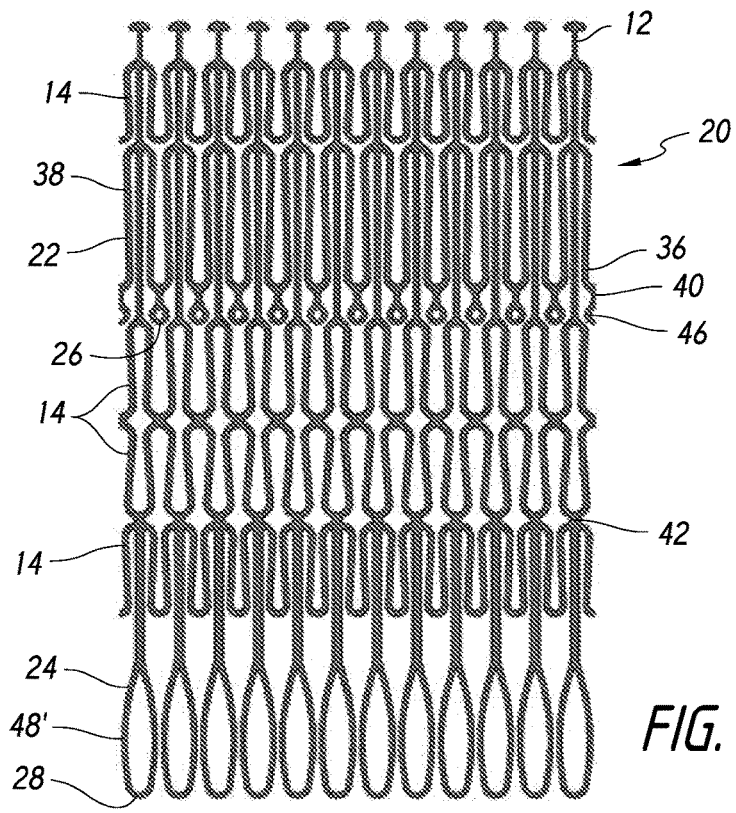
FIG. 2B is a flat pattern view of the prosthesis of FIG. 2A.

FIGS. 2A-3B show prostheses similar to that of FIGS. 1A-B with two different styles of distal anchors 24. In FIGS. 2A-B, the looped end 48' of the distal anchor is generally more elliptical with a curved tip as compared to the elongated teardrop shape of looped end 48 of FIGS. 1A-B. Otherwise the shape is substantially the same.

Figure 3A:
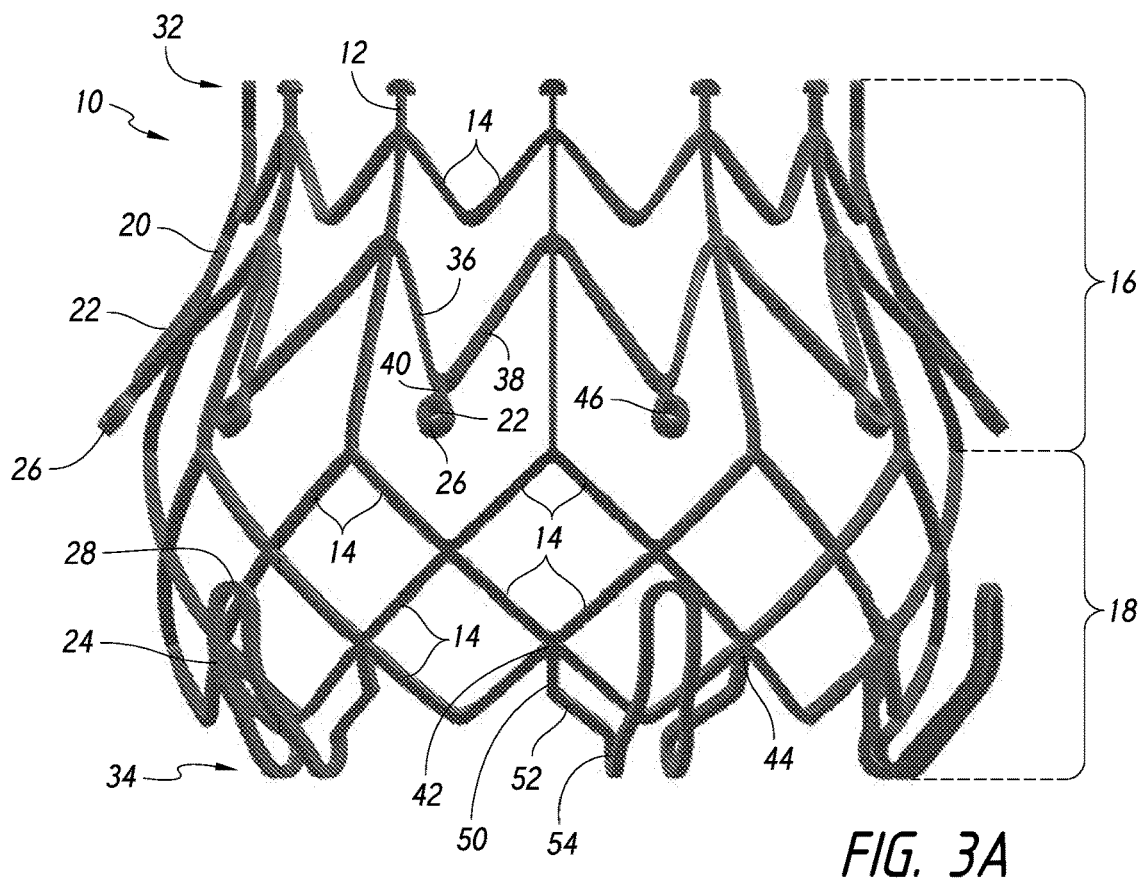
FIG. 3A is a side view of an embodiment of a prosthesis.
Figure 3B:
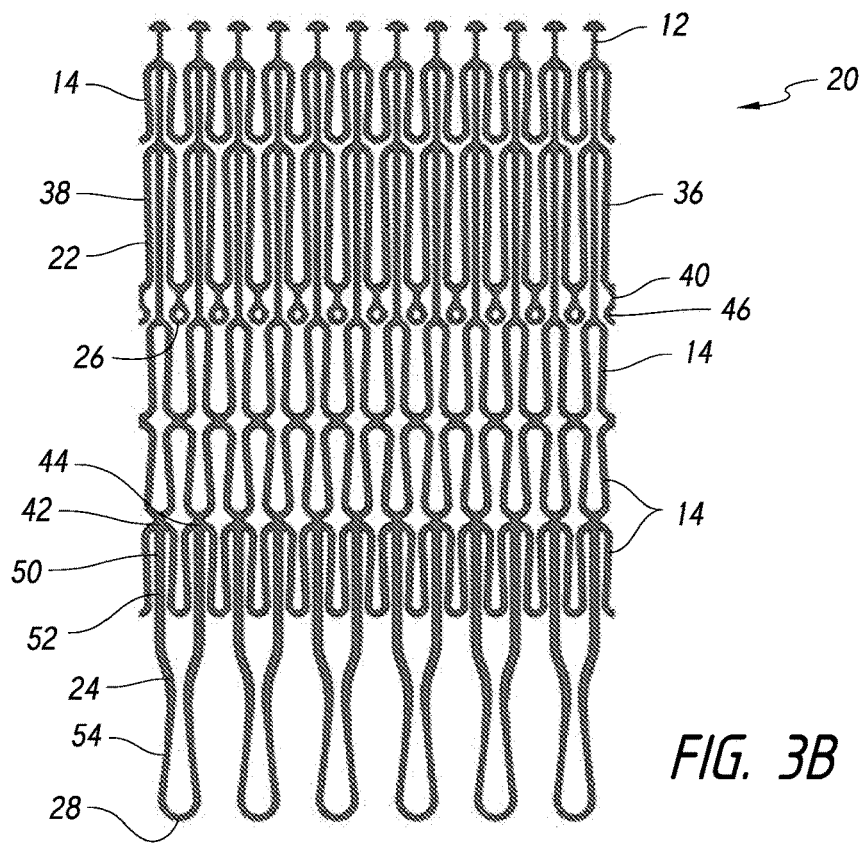
FIG. 3B is a flat pattern view of the prosthesis of FIG. 3A.

In FIGS. 3A-B, the distal anchors 24 are looped anchors rather than having looped ends. The looped anchor has a first base 42 and a second base 44 connected to the frame, wherein the first and second bases are at opposite corners of the same cell. Alternatively, the first and second bases may be located at the distal most corners of adjacent cells. The distal anchors 24 extends generally distally from the frame at the first base 42 but then is bent back around and begins to extend outwardly from the frame in a generally proximal direction. The distal anchor 24 then repeats this configuration in reverse towards the second base 44 such that the two sides of the looped anchor are mirror images of one another. It will be understood that the looped anchor can have other configurations and that it may not be symmetrical.

As illustrated in FIG. 3A, the tips 28 of the distal anchors are circumferentially aligned with the tips 26 of the proximal anchors, though in other embodiments, the tips 28 of the distal anchors may be circumferentially staggered between the tips 26 of the proximal anchors. In the embodiment of FIG. 3A, adjacent distal anchors 26 are spaced apart by one cell, though in other embodiments, adjacent distal anchors may be provided on adjacent cells. Thus, for example, instead of having six distal anchors and twelve proximal anchors as shown in FIG. 3A, there may be a 1:1 correspondence between proximal and distal anchors.

The illustrated looped distal anchor of FIGS. 3A-B is made up of the following segments. The first segment 50 extends generally longitudinally with the frame, extending distally or generally distally (e.g., slightly radially inward) with the frame. The strut is then bent so that a second segment 52 extends generally parallel with an adjacent undulating strut 14. The strut is then bent so that a third segment 54 begins to extend generally longitudinally and distally or generally distally, and then is bent back around to point in generally the opposite direction (e.g., in a proximal direction parallel or generally parallel with the longitudinal axis of the frame). The third segment 54 ends in the rounded tip 28 and then the anchor strut repeats to form the mirror image. After the third segment 54 bends back around to point in generally the opposite direction, in the embodiment illustrated the third segment may first extend radially outward at an acute angle relative to the longitudinal axis before bending into a portion that extends parallel or substantially parallel to the longitudinal axis. The paired third segments 54 extend parallel or generally parallel with one another from the second segment to the tip, though they may also move slightly towards or away from each other in some embodiments.

Figure 4:
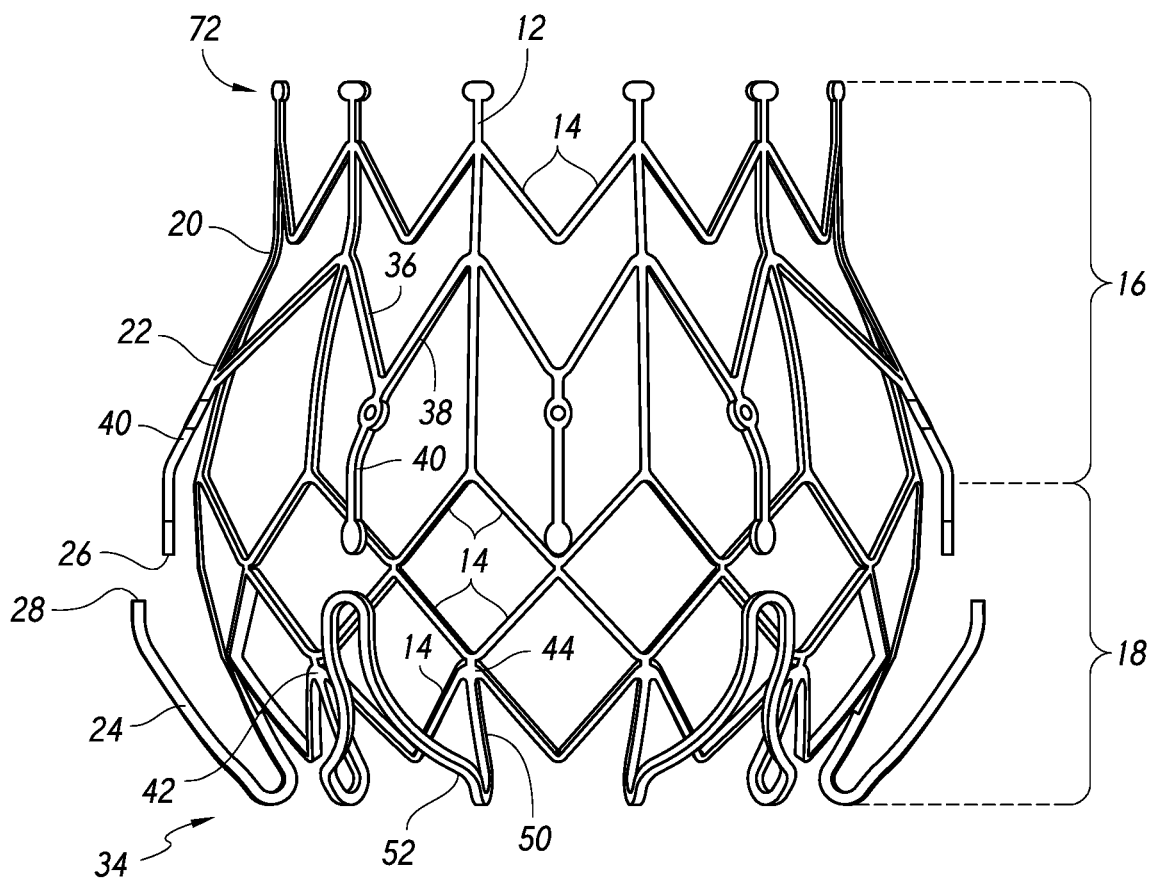
FIG. 4 is a side view of an embodiment of a prosthesis.

FIG. 4 shows a prosthesis similar to FIGS. 3A-B that also has looped distal anchors. In this embodiment the first segment 50 extends longitudinally in a distal direction from the frame and the strut is bent back on itself to point generally in the opposite (e.g., proximal) direction. The second segment is bent inward before extending parallel or generally parallel with its mirror image on the other side forming a nose and wing configuration similar to the shape of certain bicycle seats.

The proximal anchors 22 also have an elongated third strut 40. The proximal anchor 22 is shown having first 36 and second 38 struts forming a chevron and connected to longitudinal struts 12 at a base of the anchor. The first and second struts of the anchor 22 are bent at the base so that the anchor 22 extends radially outwardly from the frame as it extends towards the tip 26. The first and second struts join at a third strut 40 that continues to extend outwardly and is then bent such that the tip points distally and extends in a manner parallel or generally parallel with the longitudinal axis of the frame. The proximal anchor may or may not include an eyelet 46 along its length. The distal tip of the proximal anchors may have an atraumatic surface, such as an enlarged circular or curved end as illustrated. When the frame is in an expanded configuration, the distal anchors 24 may have tips 28 that are positioned radially outward of the tips 26 of the proximal anchors 22. Other embodiments may have the tips 26 being positioned outward of the tips 28. Such configurations are also possible with the other frames and prostheses described elsewhere herein.

Figure 5:
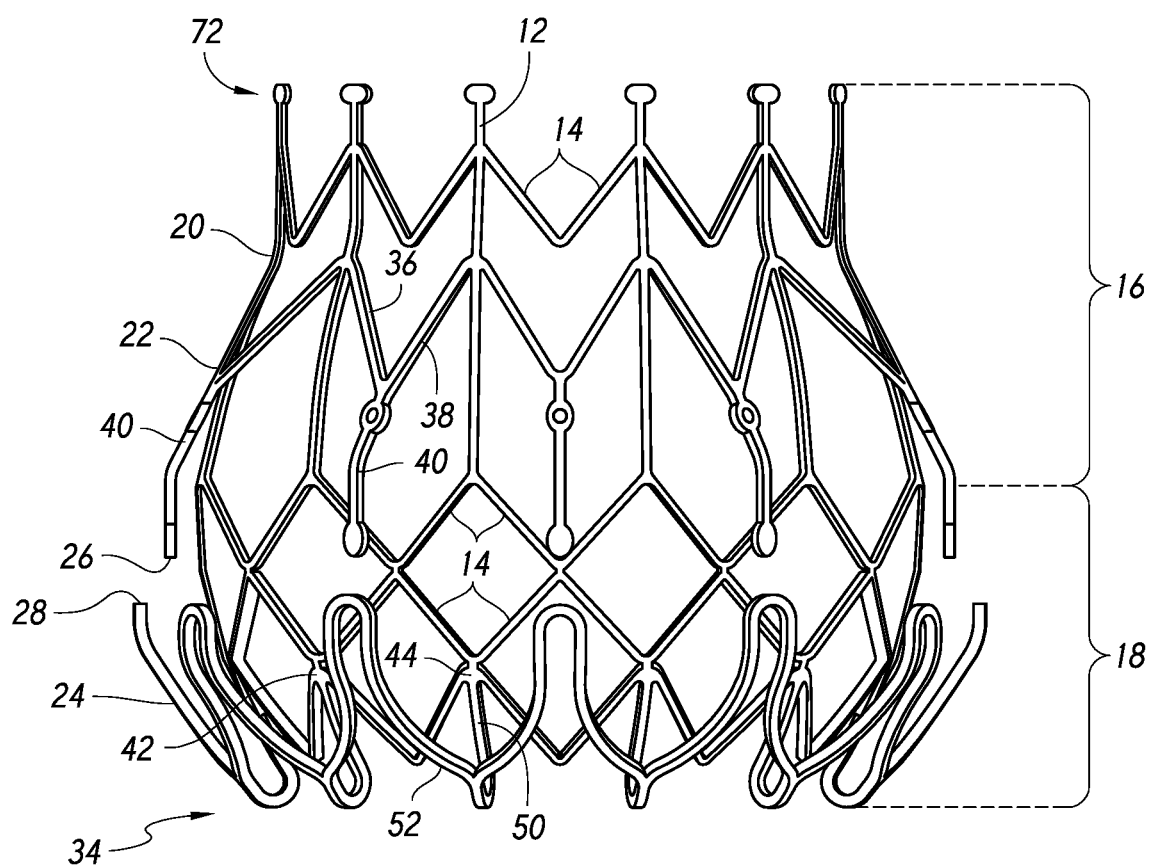
FIG. 5 is a side view of an embodiment of a prosthesis.

FIG. 5 illustrated an embodiment similar to the prosthesis of FIG. 4 with twelve distal anchors instead of six. Because of this change, in one embodiment two anchors share the first segment 50 where the anchor base 42, 44 is connected to the frame. As illustrated, each of the proximal and distal anchors may be circumferentially aligned with each other, and each of the distal anchors corresponds to one of the cells.

Figure 6A:
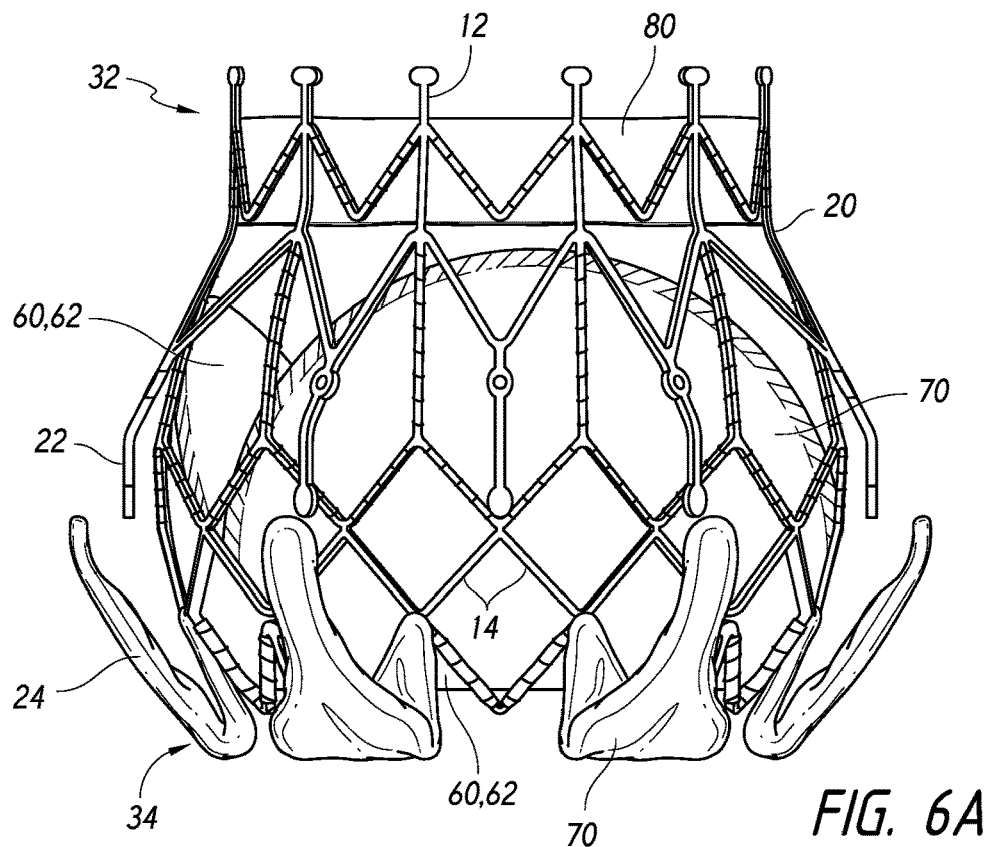
FIG. 6A is a side view of an embodiment of a prosthesis configured as a replacement heart valve.
Figure 6B:
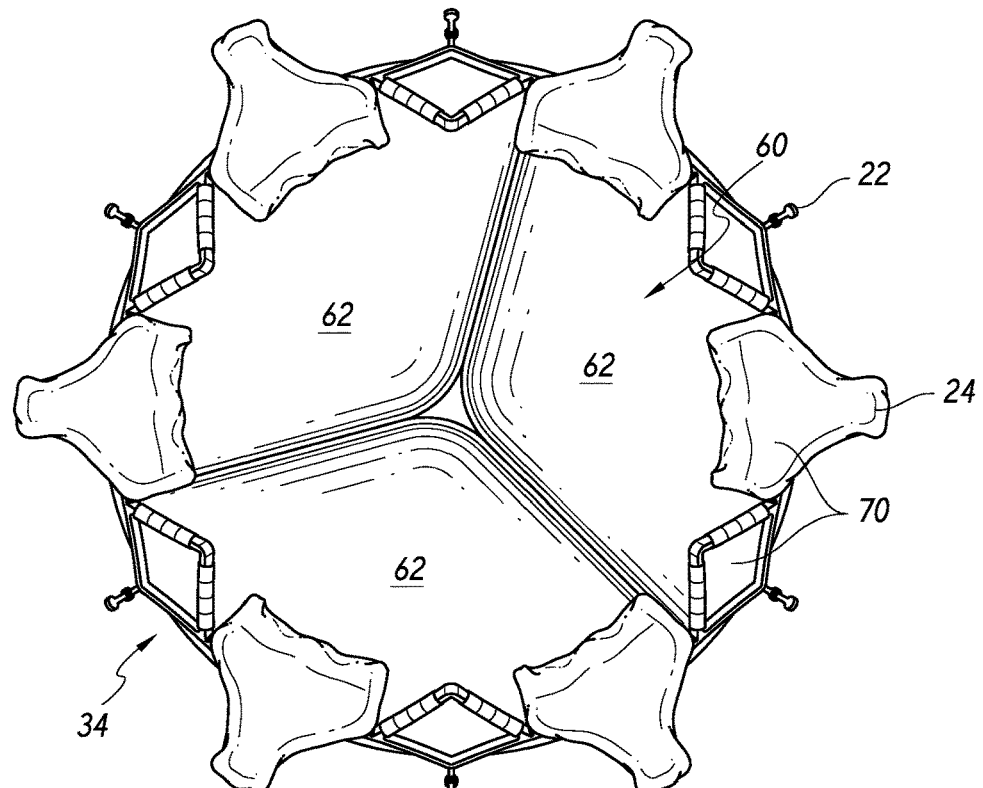
FIG. 6B is a bottom view of the prosthesis similar of FIG. 6A.

Turning now to FIGS. 6A-B, prosthesis and frame embodiments are shown similar to that of FIG. 4, including various other components of the prosthesis. A prosthesis can include one or more of a valve 60, a skirt 70 and a support band 80. The prosthesis can be a replacement heart valve similar to that and including features similar to those disclosed in U.S. patent application Ser. No. 13/165,721, filed Jun. 21, 2011, published as U.S. 2011/0313515; and Ser. No. 13/244,080, filed Sep. 23, 2011, published as 2012/0078353. The entire contents of both applications are hereby incorporated by reference herein and made a part of this specification. This is inclusive of the entire disclosure and is not in any way limited to the disclosure of the replacement heart valve.

The valve 60 can be a replacement heart valve which includes a plurality of valve leaflets 62. The plurality of valve leaflets 62 can function in a manner similar to the natural mitral valve, or to other valves in the vascular system. The plurality of valve leaflets 62 can open in a first position and then engage one another to close the valve in a second position. The plurality of valve leaflets 62 can be made to function as a one way valve such that flow in one direction opens the valve and flow in a second direction opposite the first direction closes the valve. The replacement heart valve 60 can be constructed so as to open naturally with the beating of the heart. For example, the plurality of valve leaflets 62 can open during diastole and close during systole.

In some embodiments, the leaflets 62 can be coupled to a skirt 70. For example, the proximal ends of the leaflets 62 can be connected to a proximal end of the skirt 70.

The skirt 70 can be used to at least partially control how fluid flows through and/or around the valve 60. The skirt 70 can surround at least a portion of the valve and be connected to the valve leaflets 62. In some embodiments, the skirt 70 can form an inner wall connected to and positioned within the frame 20. The skirt 70 can also be made to move with the foreshortening portion 18 of the frame 20.

The skirt 70 can extend the length of the frame 20 or it can extend along only part of the length of the frame 20. In some embodiments, the ends of the heart valve 60 can coincide with ends of the skirt 70. In addition, one or more of the ends of the frame 20 can coincide with the ends of the skirt 70. In the illustrated embodiment of FIGS. 6A-B, the proximal end of the skirt 70 and heart valve 60 are sewn together. The skirt 70 can not only extend to the distal end of the frame 20 but can also extend to the outside of the frame and is shown wrapped around each of the distal anchors 24.

Other shapes and configurations can also be used for the valve 60 and skirt 70. In some embodiments, the skirt 70 may extend along the length of the leaflets 62, but is not connected to them. In the illustrated embodiments, the skirt 70 is attached to the frame 20 and the leaflets 62 are attached to the skirt 70.

The skirt 70 can be constructed in multiple different ways. The skirt 70 can be made of knit polyester or another stretchable or flexible fabric. In some embodiments, the skirt 70 is made from a material that is more flexible than the valve leaflet material. The distal and/or proximal end of the skirt 70 can be straight, curved, or have any other desired configuration. For example, the skirt 70 is shown with undulations patterned to generally correspond to the undulations at the distal end 34 of the frame 20. It can be seen that the skirt 70 wraps around the struts at the distal end. The skirt 70 can be formed of one piece or multiple pieces. For example, the skirt 70 attached to the valve 60 can be one piece and then each distal anchor can be covered by a separate piece of material of the skirt 70. It is to be understood that other configurations of the skirt 70 can also be employed. For example, the anchors may remain uncovered, or only a portion may be covered.

Figure 7:
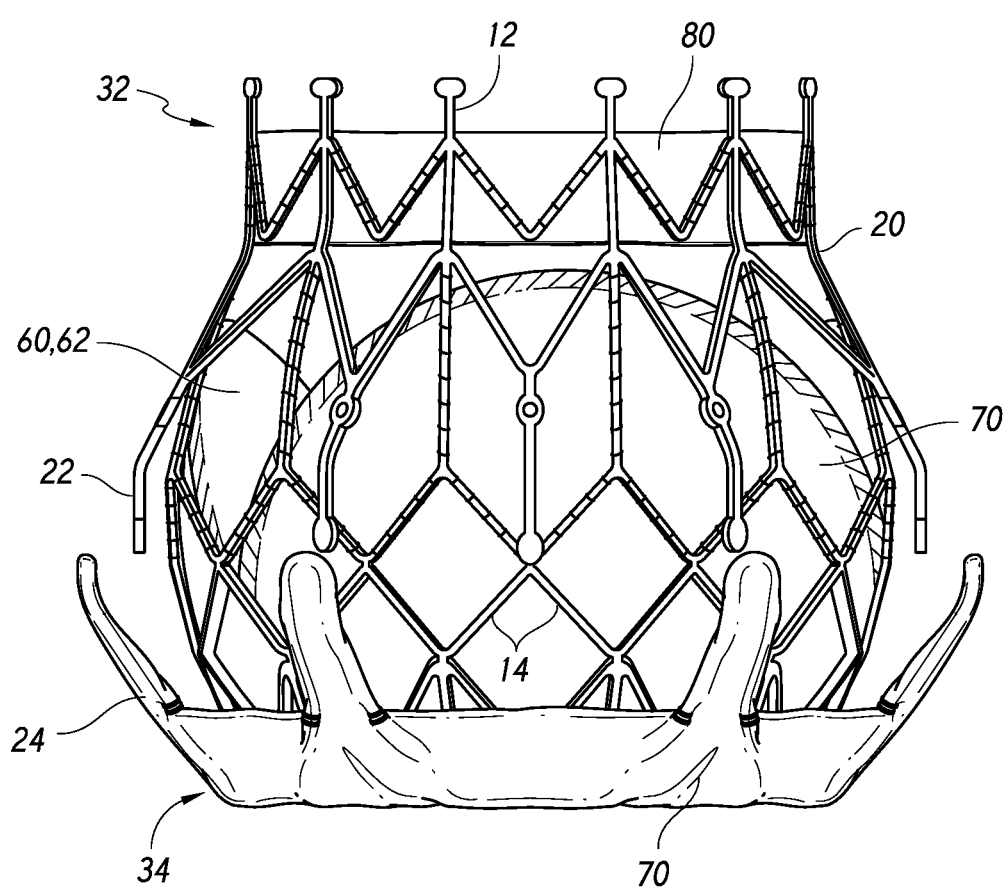
FIG. 7 is a side view of an embodiment of a prosthesis configured as a replacement heart valve.

Turning now to FIG. 7, another embodiment of the skirt 70 is shown. Here rather than the skirt 70 corresponding to the undulations at the distal end 34 of the frame 20, the skirt extends past the frame and is then wrapped around it. Thus, the skirt 70 extends from the inside of the frame 20 to the outside of the frame. The skirt can extend completely around the frame for ¼, ⅓, ½, or more of the length of the distal anchors. The skirt can also cover the distal anchors 24. In the illustrated embodiment, the skirt is a one piece skirt, but it will be understood that the skirt can be made of multiple pieces.

The skirt 70, and particularly portions that cover the distal anchors 24, can beneficially be used to help prevent leakage of blood flow around the heart valve. In addition, the skirt can encourage tissue in-growth between the skirt and the natural tissue. This may further help to prevent leakage of blood flow around the heart valve.

The prosthesis 10 can also include a support band 80 as is shown in FIGS. 6A-7. The support band 80 may be placed or positioned around or within the frame 20 at the proximal end 32. The support band 80 can be used to reinforce and/or constrain the frame 20. The support band 80 can help to control the expansion of the frame 20 from the compacted to the expanded state. The support band 80 can also be used to reduce the amount of motion that occurs at the proximal end 32 after the prosthesis 10 has been implanted at the mitral heart valve or other location.

In some embodiments, the support band 80 may comprise a polyester fabric band. The support band 80 may comprise a no-stretch or limited stretch material. Preferably the support band 80 is not made of an elastic material or a material known to have high elasticity. In some embodiments, the support band 80 is made from a material that is less flexible than the valve skirt material and/or the valve leaflet material. The distal and proximal ends of the support band 80 can be straight, curved, undulating with the undulations of frame, or any other desired configuration.

The support band 80 can be connected to the valve frame with a plurality of stitches, loops, knots, staples, or other types of connections. In some embodiments, the frame 20 can be sandwiched between two sides or layers of the support band 80. Preferably, the support band 80 is a single layer positioned within and attached to the frame 20 with a plurality of stitches around one or more of the longitudinal and/or undulating struts. In some embodiments, the support band 80 can be attached to the proximal end of the valve skirt 40.

Figure 8A:
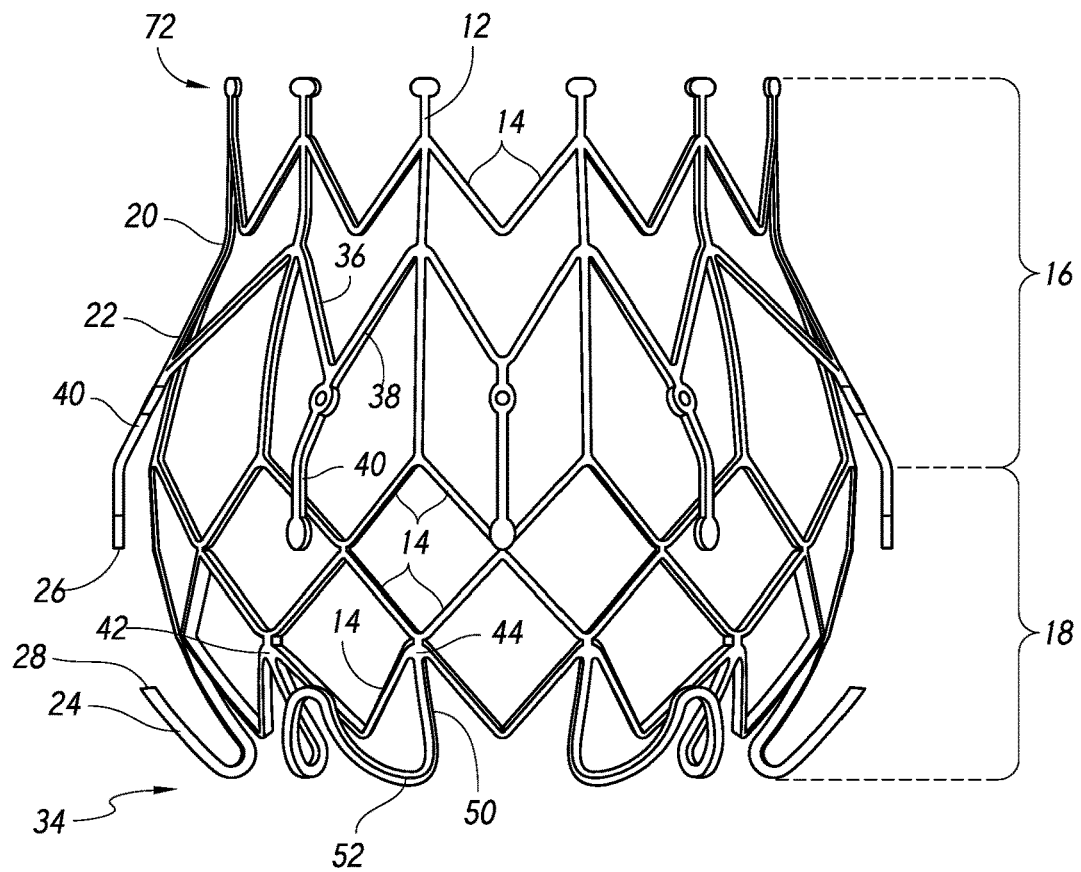
FIG. 8A is a side view of an embodiment of a prosthesis.
Figure 8B:
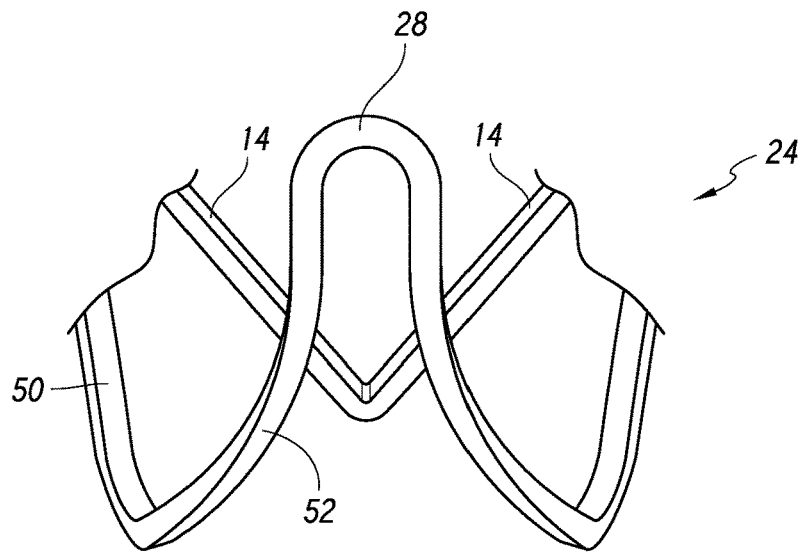
FIG. 8B is a detail view of a portion of the prosthesis of FIG. 8A.

Looking now at FIGS. 8A-B another embodiment of a prosthesis 10 is shown. FIGS. 8A-B show a prosthesis similar to that of FIG. 4 with a different style and configuration of distal anchor 24. In FIGS. 8A-B, the distal anchors are shorter than and spaced radially inward from the distal anchors of FIG. 4. Thus, as illustrated, the distal anchors 24 are not positioned as far radially outward as the proximal anchors, and the tips 28 may be positioned radially inward of the tips 26. As described further below, such a configuration may be advantageous in positioning and securing the prosthesis in a mitral valve or other body location. As shown particularly in FIG. 8B, the distal anchors 24 may comprise loops as described above, having a curved or arcuate atraumatic tip to minimize damage to body tissue.

Figure 9A:
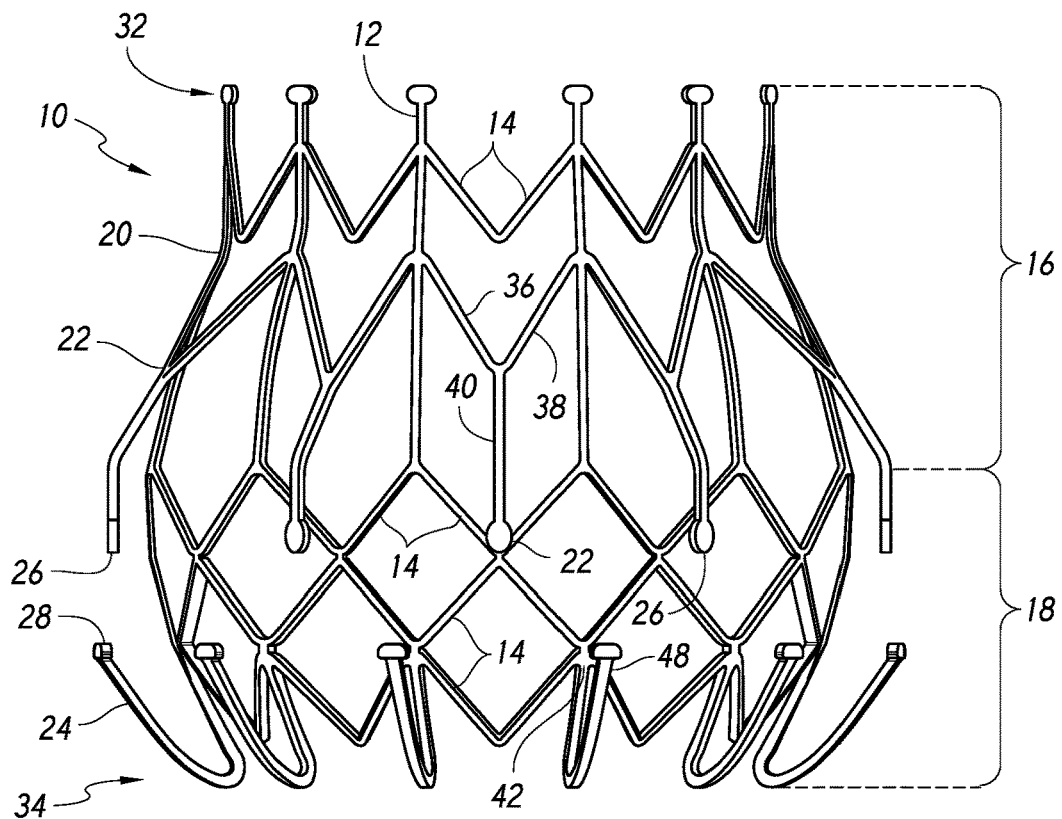
FIG. 9A is a side view of an embodiment of a prosthesis.
Figure 9B:
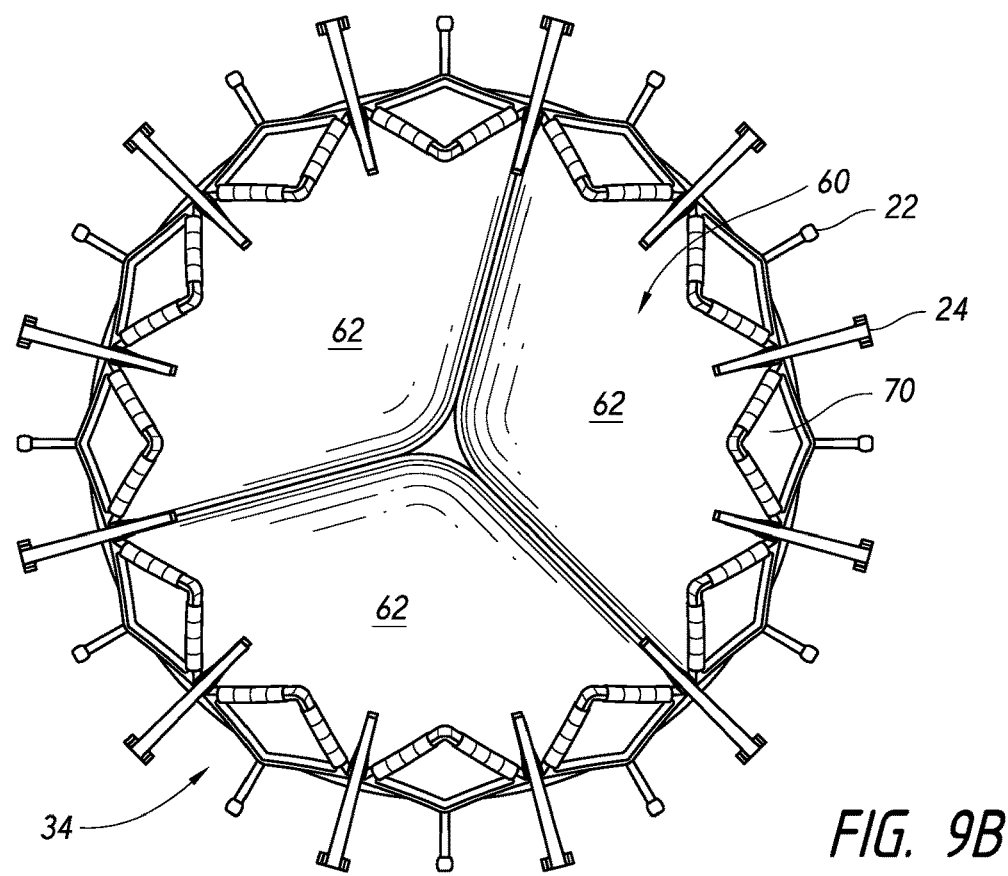
FIG. 9B is a bottom view of the prosthesis of FIG. 9A, configured as a replacement heart valve.

FIGS. 9A-B show an embodiment of a prosthesis where the distal anchors do not comprise loops, but instead comprise single struts each extending distally from the corners where adjacent cells meet. As described with respect to embodiments above, these anchors may first extend distally or generally distally, and may further extend radially inward, before bending around to extend proximally or generally proximally, such as at an acute angle relative to the longitudinal axis of the frame. The tips 28 of the anchors may comprise an atraumatic surface, such as a flattened or curved enlarged tip. As illustrated, the tips 28 may be circumferentially staggered between tips 26 of the proximal anchors 22, as best shown in FIG. 9B. FIG. 9B also shows the frame 20 having a valve 60 and skirt 70 attached as described above.

Figure 10:
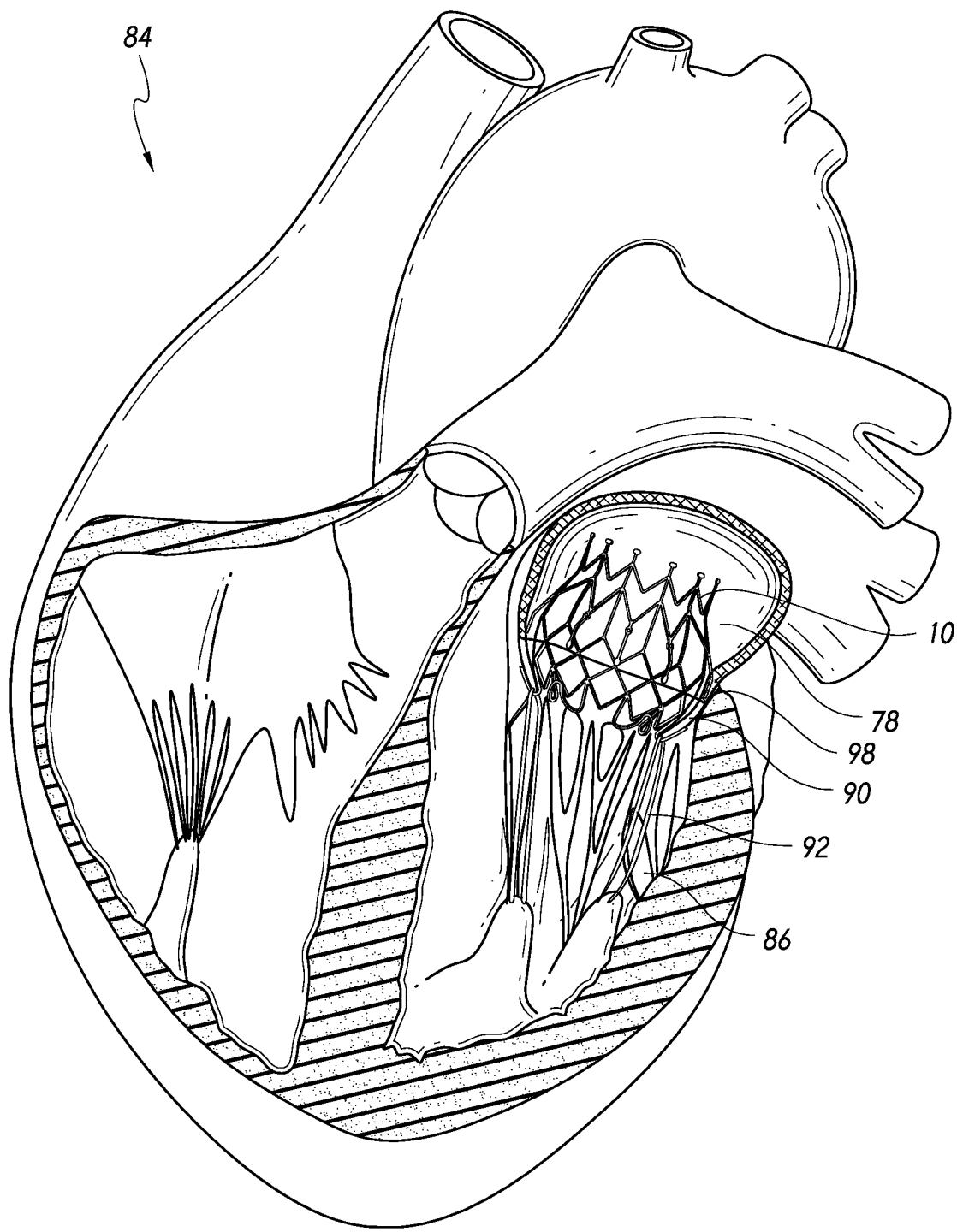
FIG. 10 is a schematic representation of a prosthesis positioned within the heart.
Figure 10A:
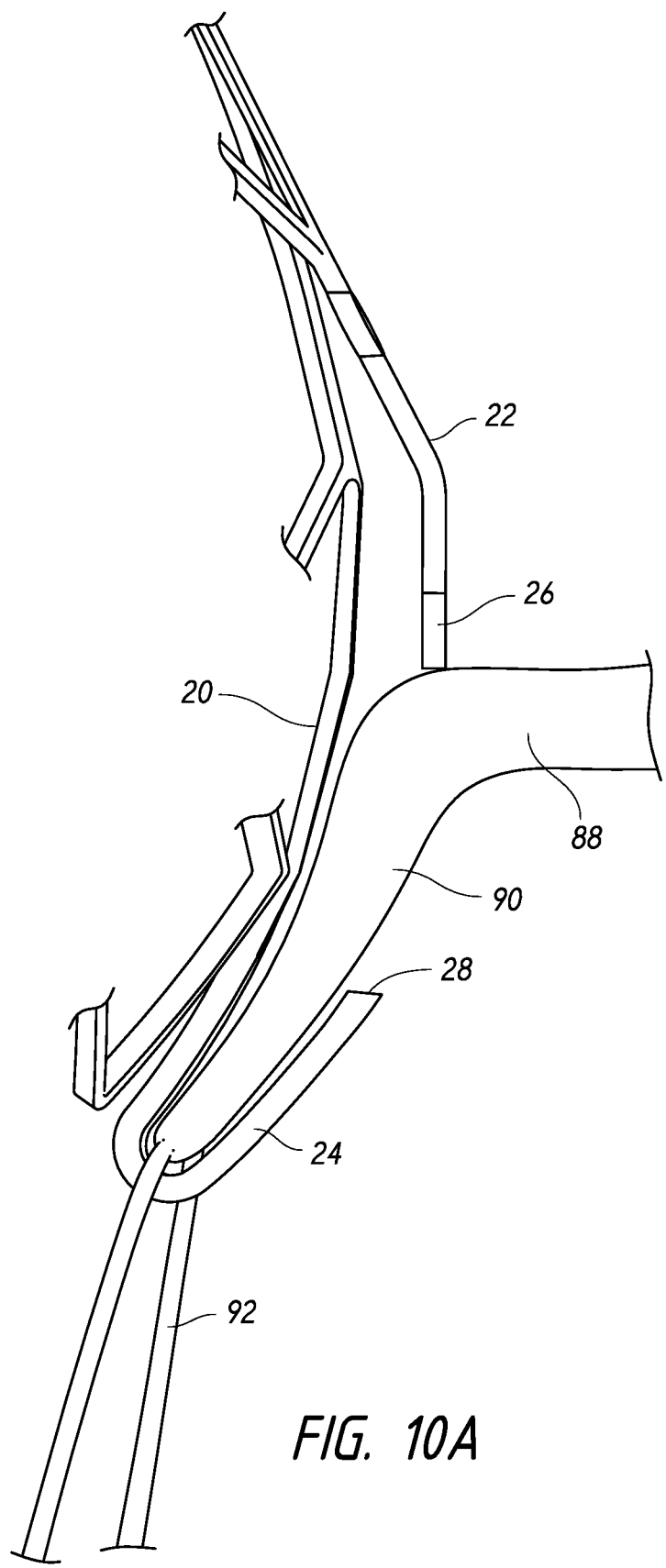
FIG. 10A is a detail schematic representation of the prosthesis positioned within the heart of FIG. 10.

In preferred embodiments, any of the prostheses 10 described above may be deployed into a heart valve annulus, and positioned when compacted so that the anchor tips 26, 28 of the opposing anchors 22, 24 are disposed on opposite sides of the native annulus 88 as shown in FIGS. 10 and 10A. As the replacement heart valve 10 is expanded, the opposing anchors are drawn closer together so as to grasp tissue on opposite sides of the native annulus 88 and securely hold the replacement heart valve 10 in position. As such, the replacement heart valve 10 can be held securely in position without requiring a substantial radial force against the native annulus. Because the anchor tips are preferably atraumatic, the grasping or engaging of tissue by the prosthesis minimizes damage to the native tissue. The foreshortening portion 18 can be used to move the anchor tips 26, 28 closer together as the replacement heart valve 10 moves to the expanded position to thereby engage the native valve annulus. The prosthesis can be deployed into a heart valve or otherwise deployed in manners similar to those described with respect to a replacement heart valve in U.S. Publication No. 2010/0298931 and 2012/0078353 the entireties of each of which are hereby incorporated by reference and made a part of this specification. This is inclusive of the entire disclosure and is not in any way limited to the disclosure related to deployment of a replacement heart valve.

FIGS. 10 and 10A show a schematic representation of the replacement heart valve 10 installed in a human heart 84. The heart is shown in cross-section, and represents typical anatomy, including a left atrium 78 and left ventricle 86. The left atrium 78 and left ventricle 86 communicate with one another through a mitral annulus 88. Also shown schematically is a native anterior mitral leaflet 90 having chordae tendineae 92 that connect a downstream end of the anterior mitral leaflet 90 and to the left ventricle 86.

In one preferred embodiment, a method is provided of delivering a replacement valve to a native mitral valve and atraumatically securing the replacement valve relative to the native mitral valve annulus 88. The replacement valve can be mounted on a delivery device and delivered to the native mitral valve annulus while the replacement valve is in a radially compacted state. The replacement valve may be positioned so that the ends or tips of the distal anchors are on a ventricular side of the native leaflets 90 beyond a location where chordae tendineae 92 connect to free ends of the native leaflets. At least a portion of the replacement valve can be released from the delivery device to thereby expand the distal anchors radially outwardly. At this time the distal anchors may extend between at least some of the chordae. The distal anchors (along with the frame) can be moved toward the ventricular side of the native valve annulus with the distal anchors extending between at least some of the chordae tendineae to provide tension on the chordae tendineae. With tension provided on the chordae tendineae, the replacement valve can be further released from the delivery device to thereby expand the proximal anchors radially outwardly. The proximal anchors upon further release of the replacement valve from the delivery device can move into engagement with tissue on an atrial side of the native valve annulus, such as with the atrial side of the native valve annulus.

The method just described may utilize any of the prostheses herein described, but may be particularly suitable for the prosthesis of FIGS. 8A-8B where the ends of the distal anchors are not positioned as far out radially as the ends of the proximal anchors when the frame is expanded. Thus, the distal anchors may have a suitable length for extending between and providing tension on the chordae tendineae, but need not and may not in some embodiments engage tissue with the tips 28. Thus, in some embodiments the some or all of the distal anchors remain spaced from tissue on the ventricular side of the native valve annulus after delivery and expansion. The interaction between the distal anchors and the chordae tendineae may therefore be sufficient to secure the distal end of the prosthesis, while the engagement of the proximal anchors with tissue on the atrial side of the native valve annulus will help further secure and orient the prosthesis As illustrated in FIGS. 10 and 10A, the distal anchors may comprise loops, such as any of the looped structures previously described. The distal anchors may also be covered with a resilient material such as described above for the skirt 70 that promotes tissue growth with adjacent body tissue. Such material may also be useful to prevent paravalvular leakage. The atraumatic distal anchors may advantageously prevent snagging of the prosthesis on internal structures, such as the papillary muscles.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

Similarly, this method of disclosure, is not to be interpreted as reflecting an intention that any claim require more features than are expressly recited in that claim. Rather, as the following claims reflect, inventive aspects lie in a combination of fewer than all features of any single foregoing disclosed embodiment. Thus, the claims following the Detailed Description are hereby expressly incorporated into this Detailed Description, with each claim standing on its own as a separate embodiment.

What is claimed is:

1. A method for deploying a self-expanding replacement valve prosthesis within a native valve having a native valve annulus, the method comprising:

advancing the self-expanding replacement valve prosthesis into a heart in a radially compacted state, the self-expanding replacement valve prosthesis comprising:
an expandable frame comprising a first end and a second end and having a longitudinal axis extending between the first end and the second end, the expandable frame configured to radially expand and contract for deployment within the native valve, wherein when the expandable frame is in an expanded configuration, the expandable frame has a larger cross-sectional dimension in a middle portion of the expandable frame and a smaller cross-sectional dimension at the first end and the second end of the expandable frame, the middle portion being between the first end and the second end;
a plurality of generally longitudinal struts extending from the first end, each of the plurality of longitudinal struts comprising a mushroom-shaped tab;
a plurality of anchors having ends positioned apart from the middle portion towards the second end, each of the plurality of anchors extending from a base attached to the expandable frame generally away from the first end before extending generally towards the first end and radially outwardly from the expandable frame, wherein each of the plurality of anchors is connected to the expandable frame at the base with a single strut which splits into two struts which connect at the end of the struts to form an atraumatic end;
a first fabric portion covering at least a portion of the second end; and
a plurality of second fabric portions each covering at least a portion of each of the plurality of anchors;
expanding the self-expanding replacement valve prosthesis to an expanded configuration; and
positioning the anchors so that at least some of the anchors are located between chordae tendineae;
wherein, after the positioning, the second end is located in a ventricle of the heart, the first end is located in an atrium of the heart, and the plurality of anchors are located on a ventricular side of the native valve annulus.

2. The method of claim 1, wherein the self-expanding replacement valve prosthesis provides tension on the chordae tendineae after positioning.

3. The method of claim 1, further comprising releasing the self-expanding replacement valve prosthesis from a delivery system.

4. The method of claim 1, wherein at least some of the plurality of anchors atraumatically contact tissue.

5. The method of claim 1, wherein the expandable frame comprises a plurality of cells formed by interconnected struts.

6. The method of claim 5, wherein the base of each of the plurality of anchors is at a location where corners of two adjacent cells meet.

7. The method of claim 5, wherein the base of each of the plurality of anchors is at a distalmost corner of a cell of the plurality of cells.

8. The method of claim 5, wherein adjacent looped ends of the plurality of anchors are spaced apart by at least one cell.

9. The method of claim 1, further comprising a valve body attached to the expandable frame.

10. The method of claim 1, wherein, when the self-expanding replacement valve prosthesis is expanded within the native heart valve, the middle portion engages the native valve annulus.

11. The method of claim 1, wherein the expanding occurs in the native valve annulus.

12. The method of claim 1, wherein a distal end of each of the plurality of anchors is covered by the plurality of second fabric portions.

13. The method of claim 1, wherein the two struts form a generally triangular loop.

14. The method of claim 1, wherein the atraumatic end is substantially flat.

15. The method of claim 1, wherein the expandable frame is bulbous.

16. The method of claim 1, wherein, after the positioning, the second end of the expandable frame curves radially inwards to form a convex curve, and each of the plurality of anchors extends in a radially inward curve to form a convex curve that generally matches the convex curve of the expandable frame.

17. The method of claim 1, wherein, after the positioning, the second end of the expandable frame tapers radially inwards and each of the plurality of anchors extends in a radially inward direction that generally matches the radially inward taper of the expandable frame.

18. The method of claim 1, wherein the replacement valve prosthesis is a replacement mitral valve prosthesis.

19. The method of claim 1, wherein the replacement valve prosthesis is a replacement tricuspid valve prosthesis.

20. The method of claim 1, wherein the replacement valve prosthesis is a replacement atrioventricular valve prosthesis.

* * * * *